(12) United States Patent
Brukalo et al.

(10) Patent No.: US 9,049,982 B2
(45) Date of Patent: Jun. 9, 2015

(54) METHODS TO PAIR A MEDICAL DEVICE AND AT LEAST A REMOTE CONTROLLER FOR SUCH MEDICAL DEVICE

(75) Inventors: Krzysztof Z. Brukalo, Chambersburg, PA (US); Manfred Ebner, Oberursel (DE); Steven Getz, Malvern, PA (US); David Hohl, Milpitas, CA (US); David Pohlman, Malvern, PA (US)

(73) Assignee: ANIMAS CORPORATION, West Chester, PA (US)

( * ) Notice: Subject to any disclaimer, the term of this patent is extended or adjusted under 35 U.S.C. 154(b) by 1106 days.

(21) Appl. No.: 13/076,319

(22) Filed: Mar. 30, 2011

(65) Prior Publication Data

US 2011/0178499 A1    Jul. 21, 2011

Related U.S. Application Data

(62) Division of application No. 11/764,081, filed on Jun. 15, 2007, now Pat. No. 8,444,595.

(51) Int. Cl.
*A61B 5/00* (2006.01)
*A61M 5/142* (2006.01)
*G06F 19/00* (2011.01)
*A61B 5/145* (2006.01)

(52) U.S. Cl.
CPC ........... *A61B 5/0002* (2013.01); *A61B 5/14532* (2013.01); *A61B 2560/0271* (2013.01); *A61M 5/14244* (2013.01); *A61M 2205/3569* (2013.01); *A61M 2205/3592* (2013.01); *A61M 2205/6018* (2013.01); *A61M 2205/6054* (2013.01); *A61M 2209/01* (2013.01); *A61M 2230/201* (2013.01); *G06F 19/3418* (2013.01)

(58) Field of Classification Search
CPC ............. A61B 5/0002; G06F 19/3418; A61M 5/14244; A61M 2005/6018
USPC .................................. 604/65–67, 890.1, 131
See application file for complete search history.

(56) References Cited

U.S. PATENT DOCUMENTS

| | | | |
|---|---|---|---|
| 4,731,051 A | * | 3/1988 | Fischell .......................... 604/67 |
| 5,665,065 A | | 9/1997 | Colman et al. |
| 6,554,798 B1 | | 4/2003 | Mann et al. |

(Continued)

FOREIGN PATENT DOCUMENTS

| EP | 2001188 A1 | 12/2008 |
|---|---|---|
| WO | WO 2007/121763 A1 | 11/2007 |
| WO | WO 2008/138006 A3 | 11/2008 |

OTHER PUBLICATIONS

U.S. Appl. No. 11/764,023 non-final rejection dated May 13, 2010, 9 pages.

(Continued)

*Primary Examiner* — Manuel Mendez

(57) ABSTRACT

A disease management system, methods, and devices are shown and described. In one embodiment, the system includes an infusion pump and a remote controller with the ability to be paired to each other. A method to verify a wireless connection between an infusion pump and a remote controller is shown and described herein. In a further embodiment, a method to verify a wireless connection between an infusion pump and a remote controller is provided. In addition, a method of operating a diabetes management system is provided in which the system includes an infusion pump and at least a remote controller.

22 Claims, 24 Drawing Sheets

(56) References Cited

U.S. PATENT DOCUMENTS

| | | |
|---|---|---|
| 6,564,104 B2 | 5/2003 | Nelson et al. |
| 6,564,105 B2 | 5/2003 | Starkweather et al. |
| 6,577,899 B2 | 6/2003 | Lebel et al. |
| 6,744,350 B2 | 6/2004 | Blomquist |
| 6,768,425 B2 | 7/2004 | Flaherty et al. |
| 6,852,104 B2 | 2/2005 | Blomquist |
| 7,025,743 B2 | 4/2006 | Mann et al. |
| 7,109,878 B2 | 9/2006 | Mann et al. |
| 7,138,089 B2 | 11/2006 | Aitken et al. |
| 7,204,823 B2 | 4/2007 | Estes et al. |
| 7,291,107 B2 | 11/2007 | Hellwig et al. |
| 7,399,277 B2 | 7/2008 | Saidara et al. |
| 7,404,796 B2 | 7/2008 | Ginsberg |
| 7,553,281 B2 | 6/2009 | Hellwig et al. |
| 2002/0193679 A1 | 12/2002 | Malave et al. |
| 2003/0060765 A1 | 3/2003 | Campbell et al. |
| 2003/0114836 A1 | 6/2003 | Estes et al. |
| 2004/0068230 A1 | 4/2004 | Estes et al. |
| 2004/0263354 A1 | 12/2004 | Mann et al. |
| 2005/0022274 A1 | 1/2005 | Campbell et al. |
| 2005/0192557 A1 | 9/2005 | Brauker et al. |
| 2005/0215982 A1 | 9/2005 | Malave et al. |
| 2005/0273080 A1 | 12/2005 | Paul |
| 2006/0122577 A1 | 6/2006 | Poulsen et al. |
| 2006/0264889 A1 | 11/2006 | Moberg et al. |
| 2007/0060870 A1 | 3/2007 | Tolle et al. |
| 2008/0206799 A1 | 8/2008 | Blomquist |
| 2008/0234992 A1 | 9/2008 | Ray et al. |
| 2008/0287922 A1 | 11/2008 | Panduro |
| 2008/0300572 A1 | 12/2008 | Rankers et al. |
| 2008/0312512 A1 | 12/2008 | Brukalo et al. |
| 2008/0312584 A1 | 12/2008 | Montgomery et al. |
| 2009/0018495 A1 | 1/2009 | Panduro |
| 2009/0069868 A1 | 3/2009 | Bengtsson et al. |
| 2009/0227855 A1 | 9/2009 | Hill et al. |
| 2009/0275886 A1 | 11/2009 | Blomquist et al. |
| 2012/0093315 A1 | 4/2012 | Nierzwick et al. |

OTHER PUBLICATIONS

U.S. Appl. No. 11/764,049 non-final rejection dated Aug. 19, 2010, 10 pages.

U.S. Appl. No. 11/764,081, non-final rejection dated Jul. 20, 2010, 10 pages, Alexandria, Virginia.

U.S. Appl. No. 11/764,081, Notice of Allowance dated Nov. 4, 2010, 6 pages, Alexandria, Virginia.

OmniPod, Insulin Management System, User Guide, Insulet Corporation, Massachusetts, 2005, 172 pages.

Paradigm Link Blood Glucose Monitor Owner's Guide, BD Consumer Healthcare, New Jersey, 2003, 40 pages.

The MiniMed Paradigm Real-Time Insulin Pump and Continuous Glucose Monitoring System, Insulin Pump User Guide, Medtronic MiniMed, 2006, 176 pages.

International Search Report issued in related International Patent Application No. PCT/US2014/054275, mailed Dec. 31, 2014, 4 pages.

Written Opinion issued in related International Patent Application No. PCT/US2014/054275, mailed Dec. 31, 2014, 5 pages.

\* cited by examiner

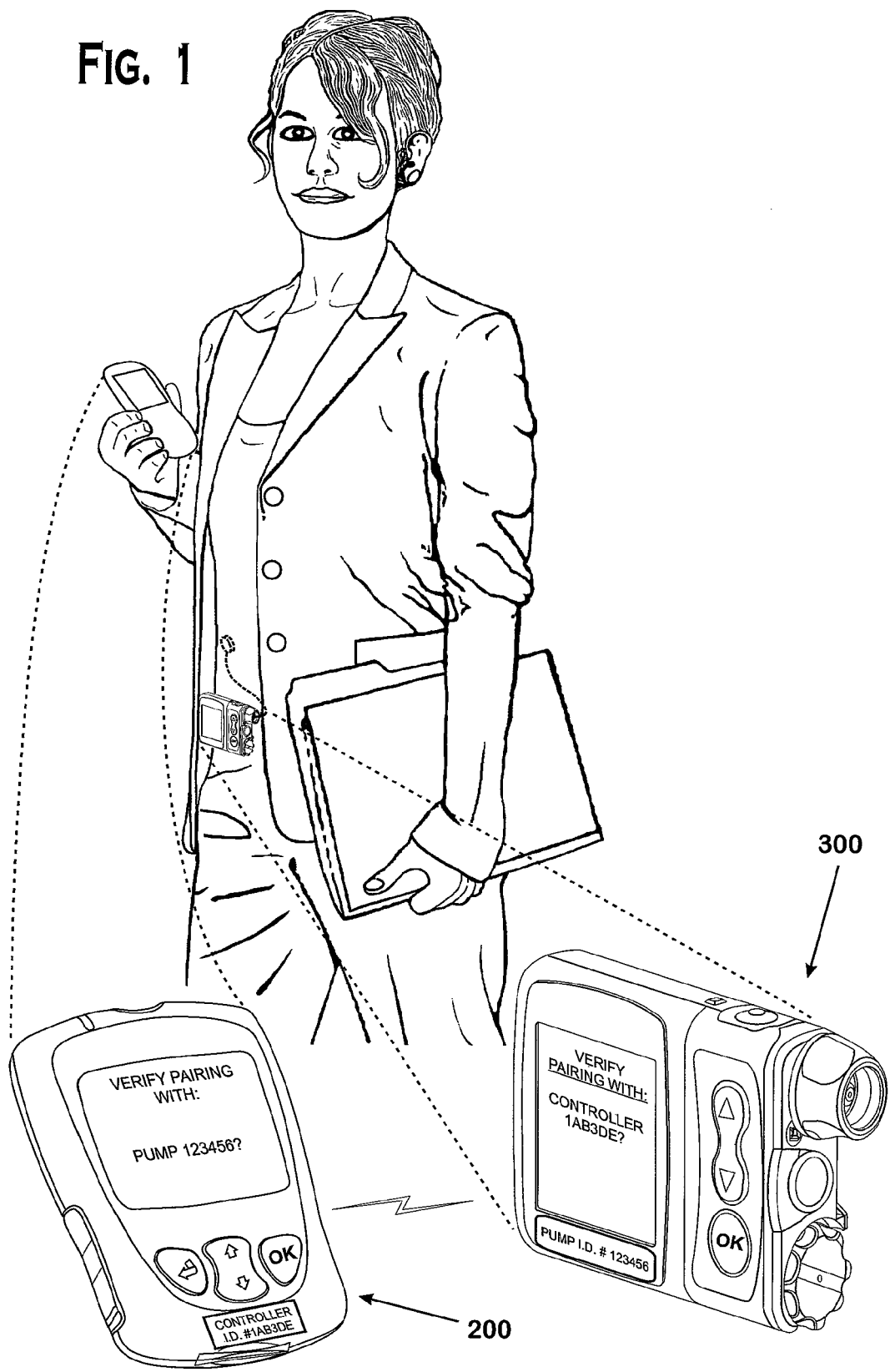

METHODS TO PAIR A MEDICAL DEVICE AND AT LEAST A REMOTE CONTROLLER FOR SUCH MEDICAL DEVICE

This application claims the benefits under 35 U.S.C. §§120 and 121 as a Divisional application of U.S. patent application Ser. No. 11/764,081, filed Jun. 15, 2007, which is now U.S. Pat. No. 8,444,585, issued May 21, 2013, which is incorporated by reference in its entirety herein this application.

BACKGROUND

External infusion devices (e.g., infusion pumps) may be used for delivering medication to users, such as insulin to diabetics. Portable external infusion devices may be attached to a user's belt, for example, or placed in a user's pocket. In external infusion devices delivering insulin, for example, the insulin may delivered via a cannula, inserted in subcutaneous tissue of the user.

Some conventional external infusion pumps may communicate remotely with another controlling device, such as a remote controller that is physically separated from the external infusion pump, for altering one or more functional settings of the external infusion pump. One example of such device is shown and described in U.S. Pat. No. 6,554,798. Another example is shown and described in US Patent Application Publication Nos. 2005/0022274 and 2005/0215982. Other conventional infusion pumps may include a remote controller with a blood glucose measurement device. One example of such device is shown and described in US Patent Application Publication No. 2004/0068230.

SUMMARY OF THE INVENTION

By utilization of various technical features described herein, the coupling or pairing of a plurality of medical devices to respective remote controllers is convenient and potentially safer for the user, and instances of incorrect device pairing are believed to be reduced. These technical features are believed to be heretofore unrecognized in the conventional system. Specifically, in one embodiment, a disease management system is provided that includes a medical device and a remote controller. The medical device includes a display for the device and having medical device identification information. The remote controller includes a controller display and remote controller identification information, in which the medical device display is configured to display the controller identification information and the controller display is configured to display the medical device's identification information when the controller and medical device are linked to each other.

In a further embodiment, a method to verify a wireless connection between a medical device and a remote controller is provided. The method can be achieved by: connecting a remote controller with a medical device via a wireless link; providing identification information specific to the medical device to the remote controller; providing identification information specific to the remote controller on the medical device; and confirming that the medical device identification is with the remote controller and that remote controller identification information is on the medical device.

In yet a further embodiment, a method of operating a diabetes management system is provided in which the system includes a medical device and at least a remote controller. The method can be achieved by: exchanging identification information of the remote controller to the medical device and identification information of the medical device to the remote controller; and permitting control of the medical device by the remote controller upon acceptance of the remote controller's identification information in the medical device and acceptance of the medical device's identification information in the remote controller.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention, in which:

FIG. 1 illustrates an exemplary operational configuration of one embodiment of the present invention.

FIG. 16B illustrates a series of display screens that can be used to provide various reports on glucose and insulin analysis;

DETAILED DESCRIPTION OF ILLUSTRATIVE EMBODIMENTS

Figure 4:
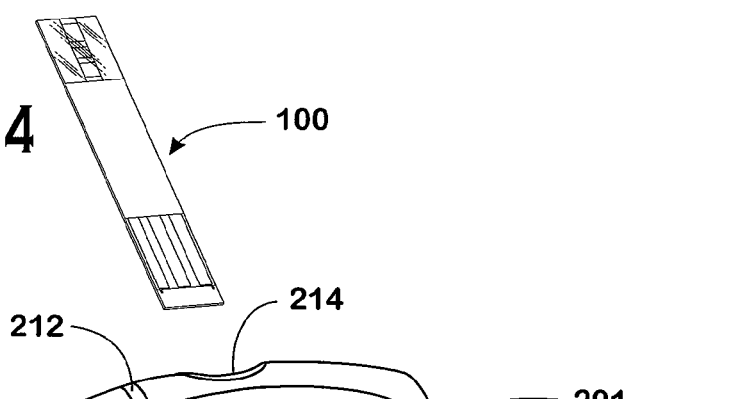
FIG. 4 is a perspective view of a test strip for use with the remote controller shown in FIGS. 2 and 3.

The following detailed description should be read with reference to the drawings, in which like elements in different drawings are identically numbered. The drawings, which are not necessarily to scale, depict selected exemplary embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Preferred embodiments described and illustrated herein are directed generally to a system having a remote controller, which may wirelessly communicate with a medical device that dispenses a fluid or medication and various methods of operation. We will describe, via the use of examples, how the remote controller and the medical device wirelessly communicate identification information with each other, how icons are used to notify a user that a wireless link that has been established between the remote controller and medical device, how similar user interfaces are used on both the remote controller and medical device, who multiple remote controllers can be paired with a medical device, how time windows are established for measured blood glucose values, and how device identification can be used with command histories.

As used herein, the terms "about" or "approximately" for any numerical values or ranges indicate a suitable dimensional tolerance that allows the part or collection of components to function for its intended purpose as described herein. In addition, as used herein, the terms "patient", "host" and "subject" refer to any human or animal subject and are not intended to limit the systems or methods to human use, although use of the subject invention in a human patient represents a preferred embodiment.

Referring to FIG. 1, an operational configuration of a remote controller 200 and a medical device 300 is shown in which the device 300 is physically connected to a user to provide monitoring of physiological parameters (e.g., heart or brain activities, body temperature, glucose level), active intervention (e.g., brain or cardiac management), or infusing of medication or bioactive agents. In the exemplary embodiments, the medical device 300 is configured as an insulin infusion pump 300, which, when placed in a wireless link with a specified remote controller 200, can indicate identification information specific to the remote controller (as "Controller 1AB3DE" which is printed or affixed to the remote controller 200). Conversely, the remote controller 200, when placed in the wireless link with the infusion pump 300, can indicate identification information specific to the infusion pump (as "Pump 123456" which is printed or affixed to the pump 300).

Thus, as configured and to be described in additional detail below, a disease management system can be configured for a chronic disease such as diabetes where the system includes a medical device, which has a display for the device and a remote controller. The remote controller has a controller display with the controller having controller identification information. In this system, the medical device display is configured to display the controller identification information, and the controller display is configured to display the medical device's identification information when the controller and medical device are linked to each other via a wireless link. As used herein, a "link" is a bidirectional communication connection using radio waves, microwave, ultraviolet, infrared or combinations thereof. In this system, the controller display includes a first screen representative of analyte measurement information and a second screen representative of an infusion pump operational information. Of note is the use of a generally common or identical user indicia and user interface for both the medical device and the remote controller. As used herein, the term "user indicia" indicates the graphical text, symbols, light or sounds and the particular arrangement of the text, symbols, light or sounds to define various functional screens (e.g., menus) to allow for programming and controlling of the controller 200 and pump 300 whereas the term "user interface" indicates the components such as buttons, switches or even a voice response interface in combination with the user indicia to allow for inputs or commands by the user. With the use of a display on the remote programmer, instructional graphics can be used to walk the user through various modes of the system, thereby making the system even more user friendly. By virtue of the system, a method is obtained in which the infusion pump and the remote controller are paired by exchanging identification information, which may include a serial number of the device; names; icons; avatars, speech identification, sounds, or combinations thereof. Also, where appropriate, the method allows for the pairing of additional remote controllers while unlinking or decoupling with any other previously paired remote controller.

Figure 2:
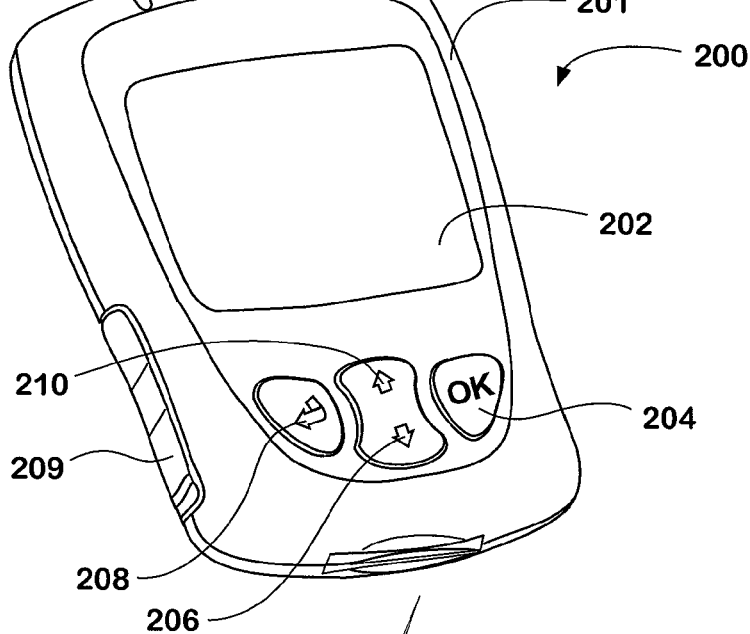
FIG. 2 is a perspective view of a remote controller shown in FIG. 1.
Figure 5:
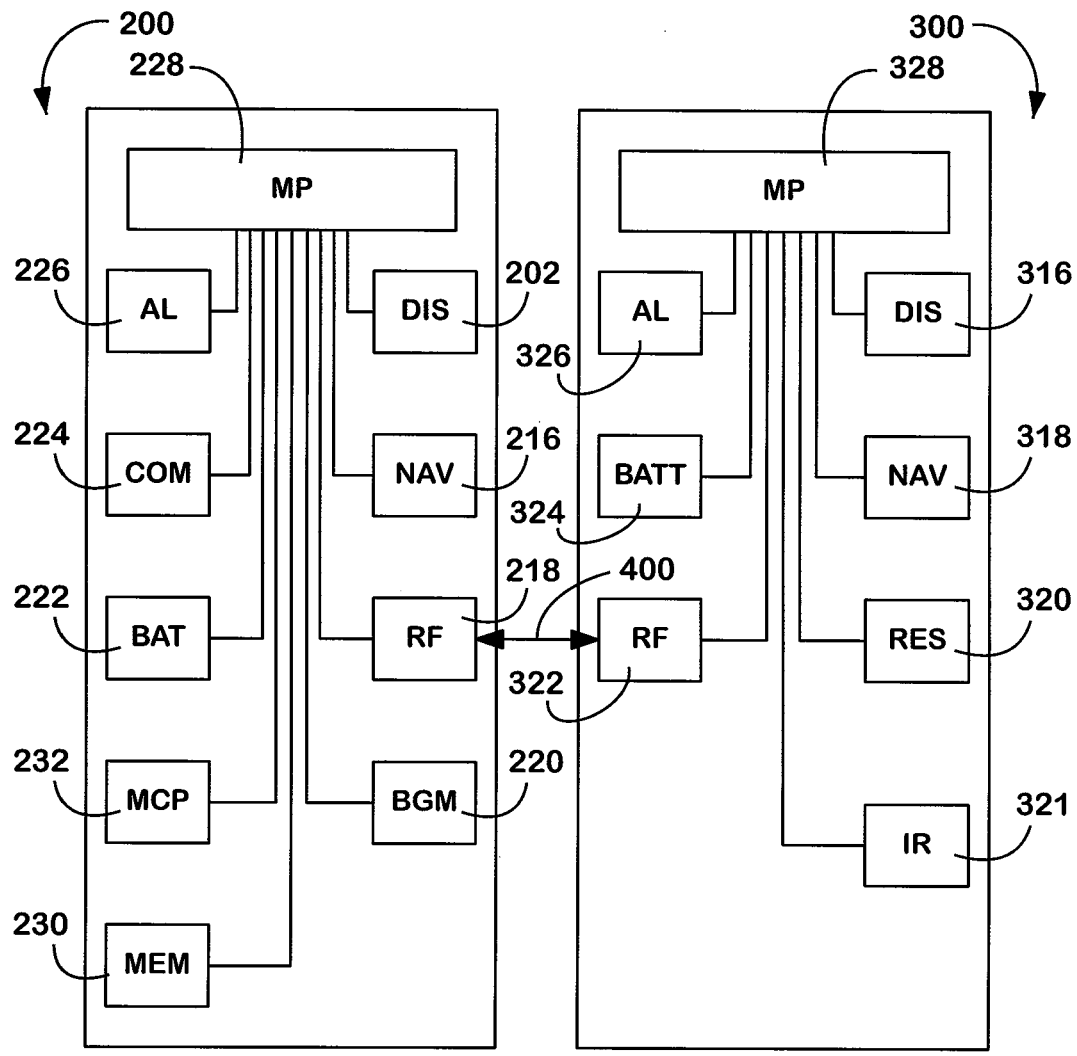
FIG. 5 is a simplified schematic view of the remote controller and the medical device exhibiting wireless communication.

FIG. 2 is a perspective view of a remote controller 200 for use in the exemplary embodiments. Remote controller 200 includes a first housing 201, a first display 202, a first OK button 204, a first down button 206, back button 208, a first up button 210, light emitting diode (LED) 212, and strip port connector (SPC) 214. Remote controller 200 is schematically shown in FIG. 5 to further include the following functional components such as a first display (DIS) 202, a first navigational buttons (NAV) 216, a first radio frequency module (RF) 218, a blood glucose measurement (BGM) module 220, a first battery (BAT) 222, a wired communication port (COM) 224, a first alarm (AL) 226, a first microprocessor (MP) 228, a memory portion (MEM) 230, and a memory chip port (MCP) 232 as shown in FIG. 5. In one exemplary embodiment, shown here in FIG. 2, a first housing 201 is ergonomically designed to be handheld and to incorporate the functional circuitry required for measuring glucose episodically and adapted to allow wireless communication with infusion pump 300.

Referring back to FIG. 2, the remote controller 200 includes a port cover 209. In one exemplary embodiment, port cover 209 is an elastomeric material that covers over a wired connection port 224 (not shown) and a memory chip port 232 (not shown). Examples of a wired connection port may be a universal serial bus (USB) or IEEE RS 232. Examples of memory suitable for insertion into memory receiving port may be a flash memory such as a SIMM card, a SmartCard, Smart Media, or any devices capable of storing data.

Referring to FIGS. 2 and 5, first display 202 may be a liquid crystal display (LCD) to show both textual and graphical information to a user. A user interface (UI) may be software driven menu that is shown on first display 202 that enables the user to operate remote controller 200. A user can navigate through the UI using first navigation buttons 216 which include first up button 210, first down button 206, first OK button 204, and back button 208. In one exemplary embodiment, the UI allows a user to operate infusion pump 300, query the status of infusion pump 300, measure glucose episodically, and to display data on first display 202 from remote controller 200 and/or infusion pump 300 (e.g. glucose concentration versus time).

First microprocessor 228 may control first display 202, first navigational buttons 216, first RF module 218, blood glucose measurement module 220, wired communication port 224, first alarm 226, and memory chip port 232. First microprocessor 228 further provides the capability to perform various algorithms for the management of a medical treatment. Examples of such algorithms may include a predictive algorithm for a user's glucose concentrations (e.g. an algorithm that predicts a user's glucose concentration in the future) and a bolus calculator. A bolus is a pre-determined amount of a medication that is dispensed over a relatively short time period. In the case of a bolus calculator, first microprocessor 228 may process inputs such as food data (e.g. carbohydrates), which may be entered manually using first navigation buttons 216, or via wired communication port 224 from a personal computer or like device. Additionally, blood glucose data may be provided to first microprocessor 228 directly from the blood glucose measurement module 220. Using the inputted food data and glucose measurement data, a bolus of insulin can be determined, and shown on first display 202, and transmit the bolus amount wirelessly from remote controller 200 to infusion pump 300. This enables infusion pump 300 to dose an appropriate amount of insulin to a user while at the same time reducing the amount of user interactions with infusion pump 300.

First RF module 218 on remote controller 200 provides for bi-directional communication to infusion pump 300 and potentially other devices such as a continuous glucose monitor, a personal computer, a personal digital assistant, a cell phone, or a second infusion pump, which may dispense glucose. Exemplary frequencies that may be suitable for use with first RF module 218 are about 433 MHz, about 863 MHz, about 903 MHz, and about 2.47 GHz. In one exemplary embodiment, first RF module 218 may include a commercially available component such as a Chipcon CC 1000, an antenna, and a RF impedance matching network. First RF module 218 may send commands to infusion pump 300 such as a basal pump rate, duration of pump, and bolus amounts. In addition, first RF module 218 may receive data from infusion pump 300 which includes an alarm indicating an occlusion or low insulin in reservoir, battery lifetime status, a continuous or semi-continuous glucose reading, and amount of remaining insulin in reservoir Wired communication port 224 provides the option of transferring data to or from an external device such as a personal computer. Wired communication port 224 may also be used to upgrade the software memory portion 230 of remote controller 200. Memory portion 230 may be a volatile memory type such as for example flash memory. Memory portion 230 may contain the application and system software for operating remote controller 200. Wired communication port 224 may then re-write memory portion 230 such that the entire application and system software is upgraded. This allows potential bugs in the software to be fixed and may be used to create added functionality in remote controller 200. In addition, a flash memory card may be inserted into memory chip port 232 for upgrading remote controller 200 without connecting it to a personal computer. Alternatively, the flash memory card may also be used for adding language support, or supplying calibration information (e.g., for a CGMS device to be paired with the controller).

Remote controller includes first alarm 226 which may be in a variety of forms to warn a user of various statuses that might need an actionable response. For example, first alarm 226 may include an audio alarm (monophonic beeps or polyphonic tones), a vibratory alarm, or a LED 212 which may be a multi-colored LED that can illuminate red, yellow, and green light. In one exemplary embodiment, an alarm signal my be used to warn a user that there is a low glucose reading, a partially filled glucose test strip, a low reservoir of insulin, an occlusion in infusion pump 300, a low battery status for infusion pump 300, a low battery status for remote controller 200, and an improperly filled test strip. For the previously mentioned situations in which a user may need to intervene because of a potentially dangerous situation, the alarm may be a vibration, audio signal, and/or LED 212 switching from green to red or from green to yellow.

Figure 3:
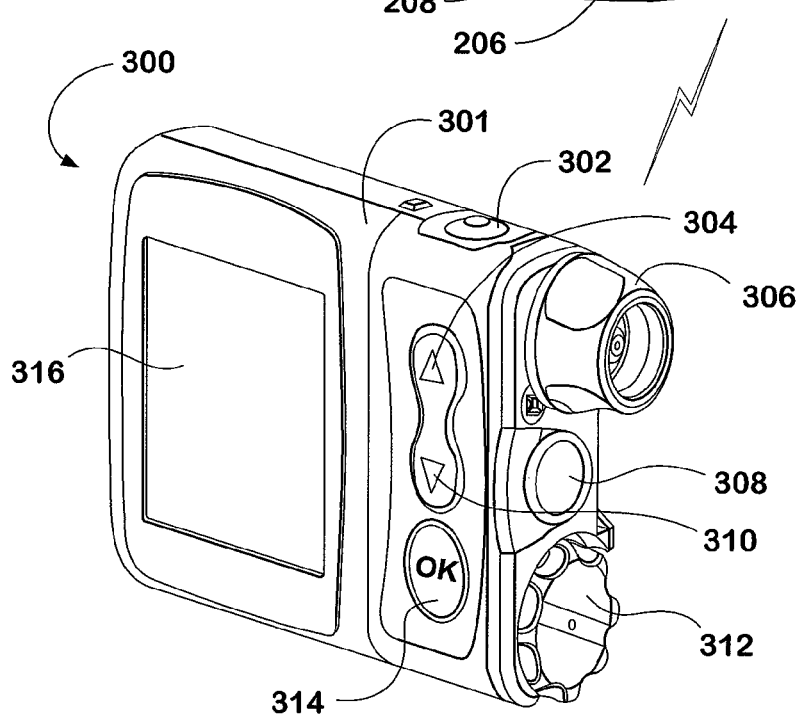
FIG. 3 is a perspective view of the remote controller shown in FIG. 1.

FIG. 3 is a perspective view of an infusion pump 300 for use in the exemplary embodiments. Infusion pump 300 includes a second housing 301, a backlight button 302, a second up button 304, a cartridge cap 306, a bolus button 308, a second down button 310, a battery cap 312, a second OK button 314, and a second display 316. Infusion pump 300 may be suitable for use in dispensing medication such as insulin for improved diabetic therapies. Similar to remote controller 200, second housing 301 may include RF transparent material and may be painted with RF transparent paint. Referring to FIGS. 4 and 5, infusion pump 300 may further include second display (DIS) 316, second navigational buttons (NAV) 318, a reservoir (RES) 320, an infrared communication port (IR) 321, a second radio frequency module (RF) 322, a second battery (BAT) 324, a second alarm (AL) 326, and a second microprocessor (MP) 328. In one exemplary embodiment, infusion pump 300 and remote controller 200 may bi-directionally communicate using a wireless signal 400 via first RF module 218 and second RF module 322. Reservoir 320 typically contains insulin that can be dispensed from infusion pump 300 via tubing and a needle attached to a user. The tubing and needle may be attached to cartridge cap 306.

Referring to FIGS. 3 and 5, in one exemplary embodiment, the antenna portion of first RF module 218 may be located within first housing 201. Similarly, second RF module 322 may be located within second housing 301. In such a case, the material used for first housing 201 and second housing 301 may be RF transparent (i.e. does not absorb or interfere with RF signals). Further, if first housing 201 or second housing 301 require that it be painted, the paint used may be RF transparent as well.

First RF module 218 and second RF module 322 further include a communication protocol that enables remote controller 200 to communicate with only a particular infusion pump 300. Both remote controller 200 and infusion pump 300 have a unique identification code embedded in their respective first RF module 218 and second RF module 322. This is desirable because under certain conditions, a second user with a second infusion pump 300 may be in close proximity to the first user. It would be undesirable for the first user's remote controller 200 to communicate with the second user's infusion pump 300. In order to avoid such a scenario, a user must initiate a pairing protocol before using infusion pump 300 for the first time. When initiating the pairing protocol, remote controller 200 and infusion pump 300 exchange their unique identification code (e.g. serial number). In all subsequent wireless communications, the correct unique identification code must be established before exchanging data.

In one exemplary embodiment, remote controller 200 may have an integrated blood glucose meter that can measure glucose episodically using disposable test strips. A test strip, which may be suitable for use in the exemplary embodiments, is the commercially available OneTouch Ultra™ test strip from LifeScan™, Inc. in Milpitas, Calif., U.S.A. A test strip 100 suitable for use in remote controller 200 is shown in FIG. 4

In addition to measuring glucose episodically, remote controller 200 can also wirelessly communicate with infusion pump 300 to provide information on the analyte measurements to the pump 300. Remote controller 200 can send commands to infusion pump 300 to dispense a fluid or medication for a pre-determined time period, rate, and/or volume. In one exemplary embodiment, a user may select from a menu of basal programs that have been programmed on infusion pump 300. In another embodiment, the user may more specifically set a basal rate, a bolus dose, and a combination thereof may be programmed as commands to infusion pump 300 from remote controller 200. Remote controller 200 can receive data from infusion pump 300 such as the status of the dispensing of medication (e.g. the dispense rate, amount of medication remaining in infusion pump 300, or the proportion of medication delivered based on the amount programmed).

Figure 6:
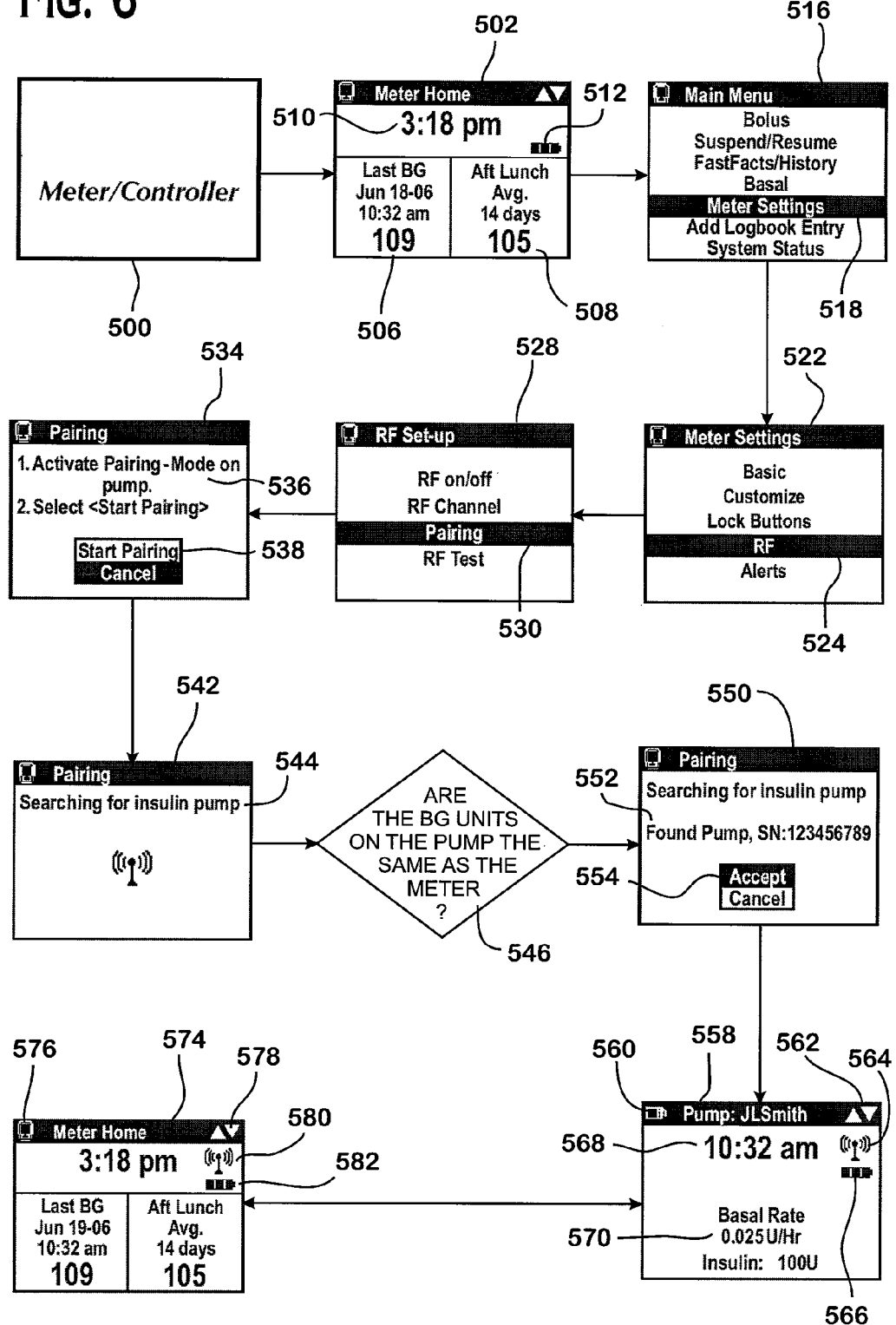
FIG. 6 is a flow chart illustrating screens for pairing a remote controller and medical device that may be displayed on the remote controller, in one exemplary embodiment.

FIG. 6 is a flow chart illustrating screens for pairing a remote controller and infusion pump that may be displayed on the remote controller, as used in the exemplary embodiments. When pairing controller 200 and infusion pump 300, the first screen is splash screen 500. Splash screen 500 is displayed when 200 is turned on. If controller 200 has not been paired to infusion pump 300, or if RF communication between 200 and infusion pump 300 is turned off, the first screen displayed after splash screen 500 is meter home screen 502. Meter home screen 502 typically includes last reading 506, average reading 508, time 510, and battery icon 512. Battery icon 512 indicates the charge in first battery 222. Pressing first OK button 204 while meter home screen 502 is displayed accesses main menu screen 516. Meter settings 518 can be highlighted by pressing first down button 206. Pressing first OK button 204 results in meter settings screen 522. RF 524 can be highlighted by pressing first down button 206, then selected by pressing first OK button 204. RF setup screen 528 is then displayed, and pairing 530 can be highlighted by pressing first down button 206 followed by first OK button 204, resulting in the display of pairing screen 534. Pairing screen 534 instructs the user to activate the pairing mode on infusion pump 300 then to highlight and select start pairing command 538. Once this is done, pairing status screen 542 is displayed, indicating pairing status 544. In the process of pairing, units criteria 546 is checked. If the blood glucose units of measure are not the same in remote controller 200 and infusion pump 300 the pairing procedure is aborted. If the blood glucose units of measure are the same in remote controller 200 and infusion pump 300, pairing result screen 550 is then displayed. Paired infusion pump 552 includes the serial number of the paired infusion pump. After verifying that paired infusion pump 552 is correct, accept command 554 is highlighted and selected. Remote infusion pump home screen 558 is then displayed, and can be toggled with meter home screen 574 by pressing first down button 206 and first up button 210. Remote infusion pump home screen 558 includes infusion pump icon 560, toggle icon 562, signal strength icon 564, battery icon 566, time 568, and delivery status 570. Infusion pump icon 560 indicates that remote infusion pump home screen 558 is a display screen that is associated with infusion pump 300. Remote infusion pump home screen 558 includes the serial number of the paired infusion pump, or alternatively can include a familiar name, assigned by the user to identify infusion pump 300, instead of the infusion pump serial number. Toggle icon 562 indicates that additional screens can be viewed by pressing first down button 206 or first up button 210. Time 568 displays the current time (a remote controller 200 setting). Signal strength icon 564 indicates RF signal strength between remote controller 200 and infusion pump 300. Battery icon 566 indicates that infusion pump 300 has a full battery charge. Delivery status 570 is an infusion pump status indicating active basal dosing and that infusion pump 300 contains 100 units of insulin. Remote infusion pump home screen 558 can be toggled with meter home screen 574 using first down button 206 and first up button 210. Meter home screen 574 includes meter icon 576, indicating that meter home screen 574 is a display screen related to remote controller 200. Meter home screen 574 includes toggle icon 578, signal strength icon 580, and battery icon 582. Toggle icon 578 indicates that additional screens can be viewed by pressing first down button 206 and first up button 210. Signal strength icon 580 indicates RF signal strength between remote controller 200 and infusion pump 300. Battery icon 582 indicates the battery charge in remote controller 200.

Figure 7:
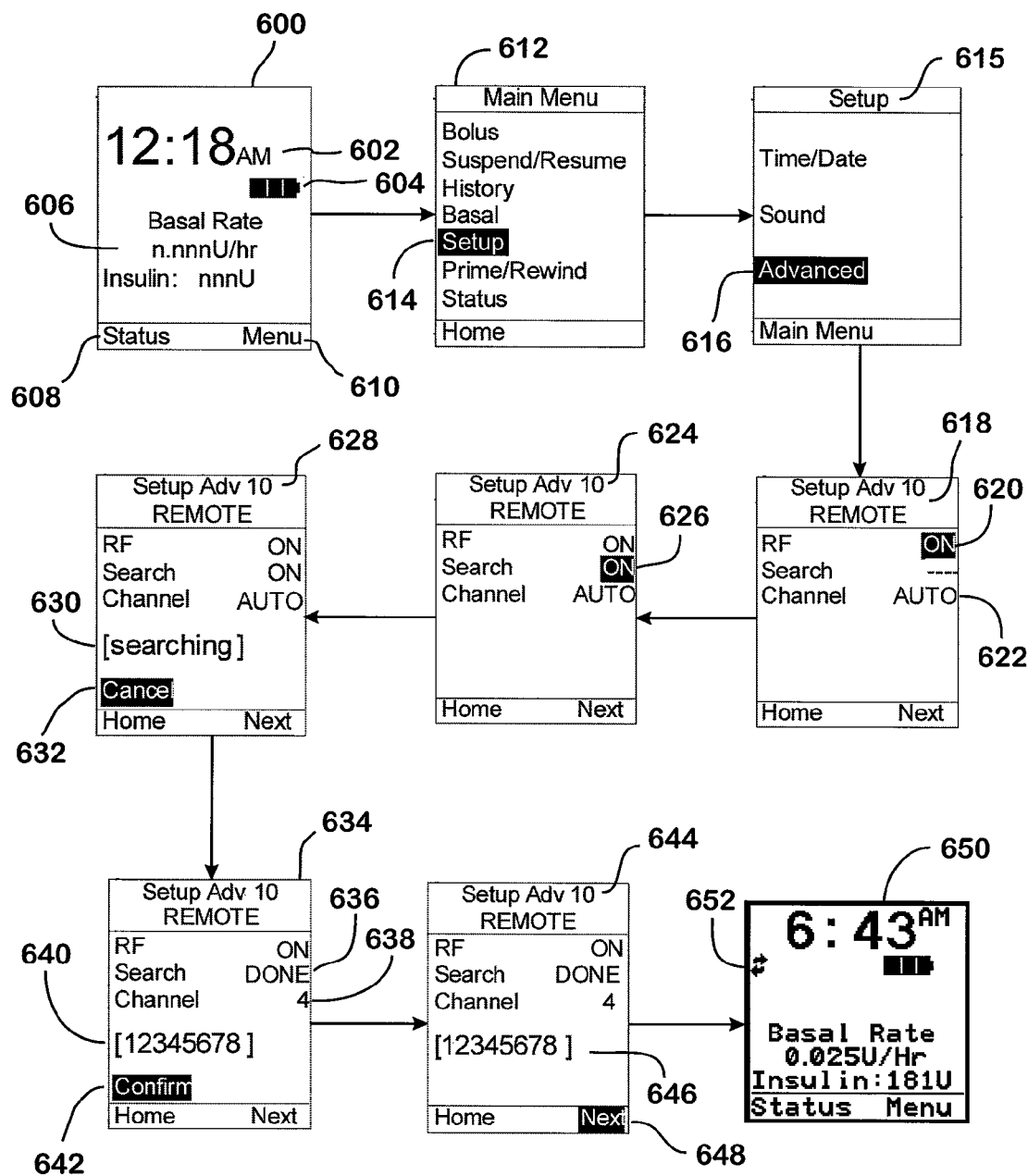
FIG. 7 is a flow chart illustrating screens for pairing a remote controller and medical device that may be displayed on the medical device in one exemplary embodiment.

FIG. 7 is a flow chart illustrating screens for pairing a remote controller and infusion pump that may be displayed on the infusion pump, as used in the exemplary embodiments. When infusion pump 300 is turned on, local infusion pump home screen 600 is displayed. Local infusion pump home screen 600 includes time 602, battery icon 604, delivery status 606, status command 608, and 610. Time 602 is the time set in infusion pump 300. This time must match the time set in remote controller 200, and displayed as time 510 in FIG. 6. Battery icon 604 indicates the battery charge in infusion pump 300. Delivery status 606 indicates the current delivery status of infusion pump 300, while status command 608 and 610 are sub-menu items related to infusion pump status and the main menu of infusion pump 300. After highlighting 610 using second up button 304 and second down button 310, second OK button 314 is pressed and main menu screen 612 is displayed. Second down button 310 can be used to highlight setup 614, and second OK button 314 is pressed to display setup screen 615. After highlighting and selecting advanced 616, remote setup screen 618 is displayed. RF 620 can be switched to on using second up button 304, second down button 310, and second OK button 314. When RF 620 is on, channel 622 is set to AUTO mode. In AUTO mode the channel for RF communication is selected automatically. In remote setup screen 624, search 626 is toggled to ON, and then remote setup screen 628 is displayed. Remote setup screen 628 includes search status 630. Search status 630 indicates that second RF module 322 is searching for compatible RF signal from other devices, such as first RF module 218. Once a device is found, remote setup screen 634 is displayed, the channel over which RF communication occurs is displayed in channel 638, and the user is prompted to confirm paired remote 640 using confirm 642. Once paired remote 640 is confirmed using confirm 642, remote setup screen 644 is displayed. Remote setup screen 644 includes paired remote 646 and next 648. By highlighting next 648 and pressing second OK button 314, display 316 displays local infusion pump home screen 650. Since infusion pump 300 is now paired with remote controller 200, remote control icon 652 is displayed. When remote control icon 652 is displayed, it indicates that RF is enabled, infusion pump 300 is paired with remote controller 200, and that infusion pump 300 is ready to receive commands from remote controller 200. Remote control icon 652 does not indicate RF traffic/activity, signal strength, or health of communications. It simply means that infusion pump 300 is enabled to receive RF commands from remote controller 200. If remote control icon 652 is not displayed on local infusion pump home screen 650 it means that RF communication between remote controller 200 and infusion pump 300 is disabled, and that infusion pump 300 will not receive commands from remote controller 200.

Figure 8:
FIG. 8 illustrates notifications that may be displayed on the remote controller during the pairing process of a remote controller and medical device in one exemplary embodiment.

FIG. 8 illustrates notifications that may be displayed on remote controller 200 during the pairing process of remote controller 200 and infusion pump 300, as used in the exemplary embodiments. Since it is important that the units of measure are the same in both bolus calculations and in historical data logs, the pairing feature will fail if the units are not identical. In some embodiments, the units can be changed by the user in both remote controller 200 and infusion pump 300. In other embodiments the units are fixed at the factory and can't be changed, in which case either remote controller 200 or infusion pump 300 are exchanged for models with compatible units of measure. In addition to units of measure, it is also important that remote controller 200 and infusion pump 300 are set to the same time. This is important in establishing when blood glucose tests were performed, and in logging events such as bolus and basal delivery. Accurate time settings are also important in monitoring averages at different times of the day.

In the exemplary embodiments, the remote controller 200 and the infusion pump 300 may incorporate a suitable radio frequency communication system, such as, for example, a far-field radio frequency communication element ("RF") for bi-directional communication. The center frequencies can be any suitable frequencies. In the preferred embodiments, the center frequencies are approximately 868 MegaHertz ("MHz") and approximately 903 MHz. The system preferably uses the Chipcon™ Product CC1100 RF Transceiver supporting frequency modulated and Frequency Shifting Keying for data transfer. Manchester encoding can be utilized to allow for self-clocking as the clock is embedded in the signal. Alternatively, Non-Return-to-Zero or NRZ encoding can also be utilized. As described above, the RF element utilizes a communication protocol that has a learn mode or "pairing" mode which pairs the two devices (remote controller 200 and infusion pump 300), in which the unique identification code of each communicating device is exchanged. Device "pairing" is a process in which a master (remote controller 200) learns who its slave is (an infusion pump) and in which the slave (infusion pump) learns who its master (remote controller) is. All devices utilize suitable information identification, such as, for example, a fixed device-type serial number address, sound, or optical identifier. Preferably, the remote controller 200 holds one serial number of the infusion pump 300 that is paired with the controller 200; the infusion pump 300 stores one single master remote controller's serial number from which it will accept commands; and only one remote controller 200 and one infusion pump 300 may be paired at a time. If a new remote controller 200 is to be "paired" to an infusion pump 300, the other remote controller 200 is "un-paired" or whose communication is ignored. During the pairing process, a communications "channel" is established for the system. The "channel" is preferably a frequency offset from the center frequency. The use of channels is believed to provide for communication that is more robust. The RF communication can be initiated by either the infusion pump 300 or the controller 200. In the preferred embodiments, the communication is initiated by the remote controller 200 (master). There is a predefined wait-listen period after the remote controller 200 transmits to the infusion pump 300, where the remote controller 200 listens for a response from the infusion pump 300. The infusion pump 300 indicates its state, if it is busy or can communicate with the remote controller 200. The remote controller 200 will then communicate with the infusion pump 300 to ask for the status (alarm, alerts, insulin units delivered, etc.) of the infusion pump, and the infusion pump will send and receive data upon request to and from the remote controller 200. The RF transmission can utilize a single frame of transmission. A frame can include a plurality of preamble or synchronization information, header and data.

In the preferred embodiments, the frame includes preamble and synchronization information, a frame header and an optional data packet with cyclic-redundancy-checksum ("CRC"). To conserve battery power, three preamble lengths may be utilized: (1) a long; (2) medium; and (3) short preambles. The long preamble is used for initiating communication, the medium preamble is used for automatic session initiation and a short preamble is used once communication is established. The predetermined number of preamble bytes to be transmitted will vary within a certain range instead of a fixed number of preamble bytes. The preamble bytes are sent before the frame to allow the RF receiver to lock and receive the frame. The variation is caused by the clock jitter of the timer, which may cause the preamble periods to be decreased or increased by about 25 milliseconds. The short and long preamble periods may be configured to account for the shortest possible variations in preamble period that could occur because of clock jitter. The buffer time period may be configured to have about the same magnitude as the clock jitter in the transmitting device. As a result, the preamble period may be about greater than or equal to the time periods for the high frequency power saving mode or the low frequency power saving mode of the receiving device. Consequently, a transmitting device may reliably and robustly send a sufficiently long preamble that will be properly received by the receiving device even if the transmitting device sends the lowest possible preamble length due to clock jitter.

The listening window scheme uses a two-stage sniff interval to optimize communication on-times. The frame header includes a command, frame number, size of the optional data packet and a CRC for the frame header. The communication protocol also incorporates a mechanism to insure that the data has been transmitted correctly by validating and verifying the transmission, this includes a use of a cyclical redundancy check and acknowledgment in the communication. For some RF commands with data packets, the associated data packet may contain the 1's complement of another data field as an added safety check for the receiver. Further, the receiver may respond to the command by repeating data fields of the initial data packet as a safety check for the originating transmitter. After the initial "pairing" has been completed, the specific address of the remote controller 200 and the infusion pump 300 are no longer transmitted as part of the data transmitted, but are contained in the CRC checksum. One example of a communication protocol and methodology that can be utilized is shown and described in International Application EP06/003650, entitled "Method For Transmitting Data In A Blood Glucose System And Corresponding Blood Glucose System," filed on Apr. 20, 2006, which application is hereby incorporated by reference in its entirety into this application herein.

Figure 9A:
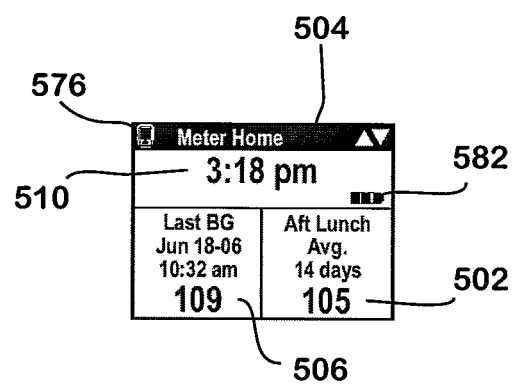
FIGS. 9A and 9B illustrate meter home screens that may be displayed on the remote controller in one exemplary embodiment.
Figure 9B:
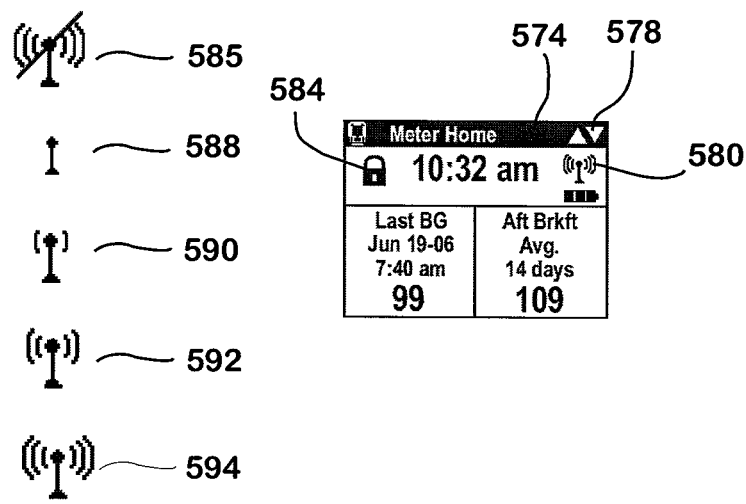

FIGS. 9A and 9B illustrate meter home screens that may be displayed on remote controller 200, as used in the exemplary embodiments. FIG. 9A illustrates meter home screen 504, a typical display before pairing, and FIG. 9B illustrates meter home screen 574, a typical display after pairing. Before pairing, meter home screen 504 includes meter icon 576, time 510, battery icon 582, last reading 506, and meter home screen 502. Meter icon 576 indicates that the screen is related to remote controller activities. Time 510 is the current time, as set in remote controller 200. Battery icon 582 indicates remaining power in remote controller 200, and can vary between empty, low, medium, and full. If battery icon 582 is empty, no functions are available in remote controller 200, and an alarm screen appears. After pairing, meter home screen 574 includes toggle icon 578, signal strength icon 580, and keys locked icon 584. Toggle icon 578 indicates that the user can switch between meter home screen 574 and remote infusion pump home screen 558 (described in reference to FIG. 10), by toggling first down button 206 and first up button 210. Signal strength icon 580 indicates the status of RF communication between remote controller 200 and infusion pump 300, and varies between RF off icon 585, RF down icon 588, low RF strength icon 590, medium RF strength icon 592, and full RF strength icon 594. If no infusion pump is paired, signal strength icon 580 is not shown. Keys locked icon 584 indicates that the user interface has been locked, and only limited functionality is available, preventing inadvertent activation of controller and infusion pump functions.

Figure 10:
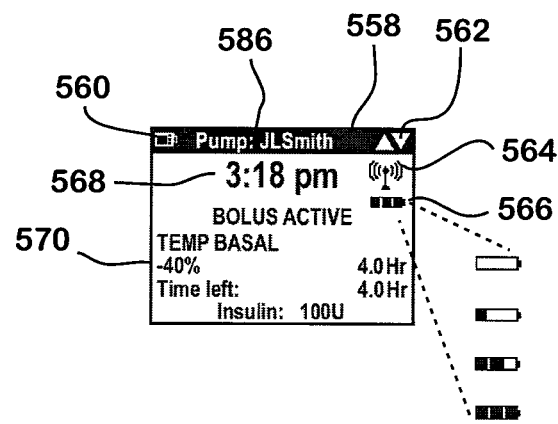
FIG. 10 illustrates a medical device home screen that may be displayed on the remote controller in one exemplary embodiment.

FIG. 10 illustrates an infusion pump home screen that may be displayed on remote controller 200, as used in the exemplary embodiments. Remote infusion pump home screen 558 is only displayed on remote controller 200 if remote controller 200 is paired to infusion pump 300. When remote controller 200 is paired to infusion pump 300, the user can toggle between remote infusion pump home screen 558 and meter home screen 574 (illustrated in FIG. 9B) by pressing first down button 206 or first up button 210 on remote controller 200. Remote infusion pump home screen 558 includes remote infusion pump home screen 586, indicating the serial number or friendly name of infusion pump 300 with which remote controller 200 is paired. By default, remote infusion pump home screen 586 includes the serial number of infusion pump 300 with which remote controller 200 is paired. The serial number displayed on remote infusion pump home screen 586 can be checked against the serial number printed on the back of infusion pump 300. To make remote infusion pump home screen 586 more recognizable to the user, the identifying information in infusion pump 300 can be programmed to display a more common name in remote infusion pump home screen 586 such as "Harold's infusion pump." The common name displayed on remote infusion pump home screen 586 can include a common name only, a common name along with a serial number, or only the serial number, as in the preferred embodiments. This makes it easier for a user to confirm correct pairing between remote controller 200 and infusion pump 300. In alternative embodiments, other identifiers can be used to help the user in confirmation of correct pairing. Those embodiments can included user programmed computer icons, computer avatars, names, sounds, or pictures. Whenever a user displays remote infusion pump home screen 558, user programmed computer icons, computer avatars, names, sounds, or pictures can be displayed, indicating to the user correct pairing between remote controller 200 and infusion pump 300. The identifying information in infusion pump 300 can be entered directly into infusion pump 300 by way of its keyboard, or it can be downloaded from a personal computer. Identifying information can also be added to remote controller 200, and can be displayed whenever remote controller 200 is turned on and remote controller related screens are displayed, such as meter home screen 574. Remote infusion pump home screen 558 also includes infusion pump icon 560, toggle icon 562, signal strength icon 564, battery icon 566, time 568, and delivery status 570. Infusion pump icon 560 is an icon that indicates to the user that they are viewing an infusion pump related screen. Toggle icon 562 indicates to the user that they can switch between remote infusion pump home screen 558 and meter home screen 574 (illustrated in FIG. 9B) by pressing first down button 206 or first up button 210. Signal strength icon 564 indicates the status of RF communication between remote controller 200 and infusion pump 300, as described previously in respect to signal strength icon 580 (in FIG. 9B). Battery icon 566 indicates remaining power in infusion pump 300, and can vary between empty, low, medium, and full. If battery icon 566 indicates no remaining power in infusion pump 300, no functions are available in infusion pump 300, and an alarm screen appears. Time 568 is the current time, as entered in remote controller 200 and infusion pump 300. Delivery status 570 indicates the delivery status of infusion pump 300, and the remaining insulin in infusion pump 300.

Figure 11:
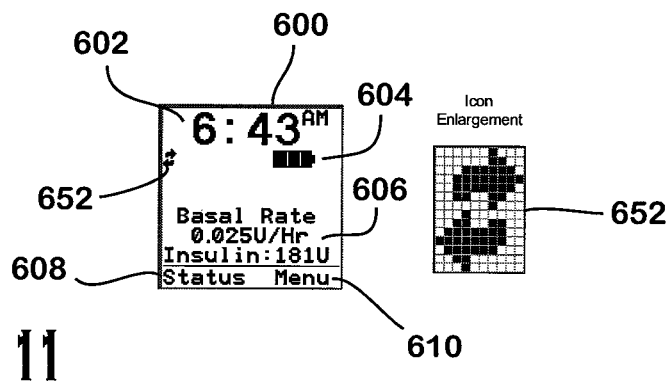
FIG. 11 illustrates a medical device home screen that may be displayed on the medical device in one exemplary embodiment.

FIG. 11 illustrates an infusion pump home screen that may be displayed on the infusion pump 300, as used in the exemplary embodiments. Local infusion pump home screen 600 differs from remote infusion pump home screen 558 (illustrated in FIG. 10) in that local infusion pump home screen 600 is displayed on infusion pump 300, while remote infusion pump home screen 558 is displayed on remote controller 200. In systems that include both remote controller 200 and infusion pump 300, and where commands entered on remote controller 200 can control infusion pump 300, it is desirable to have user interface screens on both remote controller 200 and infusion pump 300 which allow manipulation and control of features on infusion pump 300, such as basal delivery, bolus delivery, infusion pump status, and infusion pump history. In systems that use infusion pump home screens on both remote controller 200 and infusion pump 300, it is desirable to use user interface elements that are common on both screens, as can be seen in local infusion pump home screen 600 and remote infusion pump home screen 558. Using common user interface elements makes it intuitive for a user to control infusion pump 300 locally, by using local infusion pump home screen 600, or remotely, by using remote infusion pump home screen 558. In alternative embodiments, local infusion pump home screen 600 can include identifying information, such as the serial number of infusion pump 300, or a friendly name or recognizable name, such as "Harold's infusion pump." Identifying information can help in assuring to a user that they are using the correct infusion pump 300. Returning to FIG. 11, local infusion pump home screen 600 includes time 602, battery icon 604, delivery status 606, status command 608, 610, and remote control icon 652. Battery icon 604 indicates remaining power in infusion pump 300, and can vary between empty, low, medium, and full. If battery icon 604 is empty, no functions are available on infusion pump 300, and an alarm screen appears. Battery icon 604 on local infusion pump home screen 600 is similar in function and appearance to battery icon 566 on remote infusion pump home screen 558, maintaining consistency in the user interface of remote controller 200 and infusion pump 300. Time 602 displays the current time, as entered in the setup of infusion pump 300. It is similar in appearance and function to time 568 on remote infusion pump home screen 558. Delivery status 606 indicates the current delivery mode and remaining insulin in infusion pump 300. Delivery status 606 is similar in appearance and function to delivery status 570 on remote infusion pump home screen 558. Status command 608 is a submenu, and allows access to a series of infusion pump status screens. 610 is a submenu that allows access to the infusion pump main menu. Remote control icon 652 is an icon that indicates the infusion pump is under remote control. When remote control icon 652 is displayed, RF communication between remote controller 200 and infusion pump 300 is enabled, remote controller 200 and infusion pump 300 have been paired, and infusion pump 300 is ready to receive remotely entered commands from remote controller 200. In some embodiments, this icon does not indicate RF traffic/activity, signal strength, or health of communications, as other icons do (such as signal strength icon 564 in FIG. 10, signal strength icon 580 in FIG. 9B, which have been described previously). In other embodiments, remote control icon 652 can include indication as to RF traffic/activity, signal strength, or health of communications, or one can also include an icon such as signal strength icon 564 or signal strength icon 580 near remote control icon 652. Alternatively, one can also include an icon that looks like an infusion pump, indicating to the user that local infusion pump home screen 600 is related to infusion pump functions. This can be particularly useful in systems that include remote controller 200 and infusion pump 300, in that a user can get confused as to the function of various screens.

Figure 12:
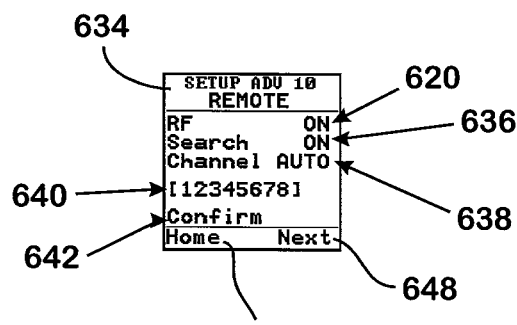
FIG. 12 illustrates a medical device setup screen that may be displayed on the medical device in one exemplary embodiment.

FIG. 12 illustrates an infusion pump setup screen that may be displayed on infusion pump 300, as used in the exemplary embodiments. Remote setup screen 634 includes RF 620, search 636, channel 638, paired remote 640, confirm 642, next 648, and home 654. RF 620 allows a user to enable or disable RF communication between infusion pump 300 and remote controller 200. When RF 620 is toggled to on, RF communication between infusion pump 300 and remote controller 200 is enabled. When RF 620 is toggled to off, RF communication between infusion pump 300 and remote controller 200 is disabled. If infusion pump 300 is currently paired with remote controller 200 when RF 620 is toggled to off, pairing data is preserved so it can be restored when RF is re-enabled. If remote controller 200 is currently attempting to pair when RF 620 is toggled to off, the pairing attempt is aborted, and previous pairing data is restored, if available. When RF 620 is toggled to "ON" and infusion pump 300 was previously paired to remote controller 200, infusion pump 300 automatically begins pairing to the previously paired remote controller 200. If infusion pump 300 was not previously paired to remote controller 200, infusion pump 300 prepares itself to be paired for the first time. Search 636 is used to initiate pairing between infusion pump 300 and remote controller 200. When search 636 is blank, infusion pump 300 is not paired with remote controller 200, and it does not contain pairing data. This is the state of infusion pump 300 when it is turned on for the first time. Unlike remote controller 200, once infusion pump 300 is paired, there is no means to un-pair it. When search 636 is "ON", pairing between infusion pump 300 and remote controller 200 has begun, and is in process. When search 636 is "DONE", the pairing search between infusion pump 300 and remote controller 200 has ended, as a result of successful pairing, or as a result of aborted pairing. Channel 638 indicates the method for selecting the channel over which RF communication between infusion pump 300 and remote controller 200 will occur. When set to "AUTO", the software in infusion pump 300 determines the RF channel. Alternatively, the user can select a channel over which RF communication occurs, such as 1-16. Paired remote 640 displays the pairing status between infusion pump 300 and remote controller 200. When paired remote 640 is blank, infusion pump 300 is not paired with remote controller 200. When paired remote 640 displays "searching", infusion pump 300 is attempting to pair with remote controller 200. When infusion pump 300 has paired with a device, the device provides confirmation such as, for example, a series of tone, a display or other visual indicators. In the preferred embodiments, the paired remote 640 displays the serial number or other identifying information (such as a name, computer icon, sounds or series of tones/vibrations, etc.) of the device, this allows the user to easily check that they have paired with the appropriate device, particularly if the identifying information is familiar, such as "Bob's remote Controller". If paired remote 640 displays the serial number of the paired device, such as remote controller 200, it can be checked against the serial number printed on the back of the paired device. Confirm 642 is a command that allows the user to confirm RF connection between infusion pump 300 and a paired device, such as remote controller 200. If a pairing search is under way, confirm 642 displays a cancel command, in case the user wants to cancel the pairing search. If confirm 642 displays a confirm command, and it is not executed by the user, the pairing between infusion pump 300 and remote controller 200 is rejected. This allows a user to reject pairing with the wrong device, such as someone else's infusion pump.

Figure 13:
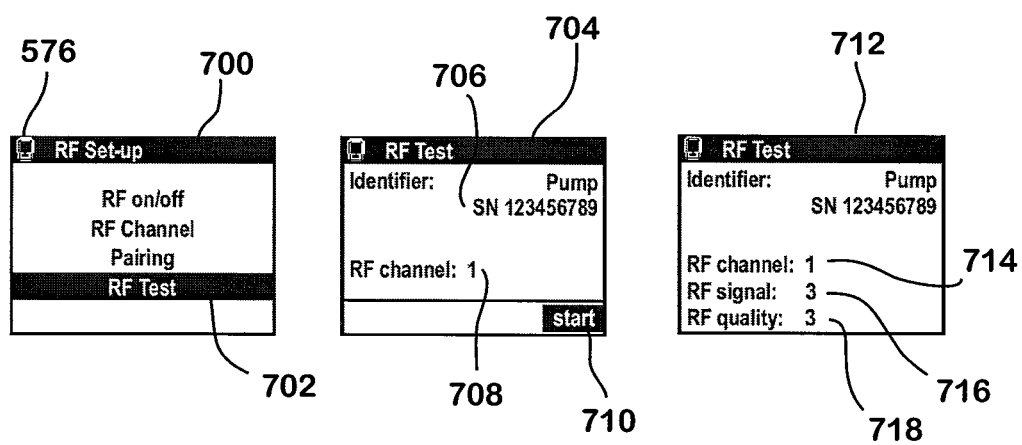
FIG. 13 illustrates RF communication setup and test screens that may be displayed on the remote controller in one exemplary embodiment.

FIG. 13 illustrates RF communication setup and test screens that may be displayed on the remote controller 200, as used in the exemplary embodiments. RF set up screen 700 is displayed on remote controller 200, and is a remote controller related screen, as indicated by meter icon 576. By highlighting and selecting RF test 702, RF test screen 704 is displayed. RF test screen 704 includes identification 706, RF channel 708, and start 710. Identification 706 identifies the infusion pump 300 with which remote controller 200 is paired, and can be in the form of a serial number, a name, or other identifying feature, as mentioned previously. RF channel 708 identifies the RF channel over which remote controller 200 communicates with infusion pump 300, and was selected either automatically by remote controller 200 and infusion pump 300 during pairing, or was selected for optimum signal and reception by the user. Start 710 is a command that initiates the start of an RF test. RF test screen 712 displays the result of the test, and includes RF channel 714, RF signal 716, and RF quality 718. RF channel 714 identifies the channel over which RF communication occurs between remote controller 200 and infusion pump 300, RF signal 716 identifies the strength of the RF signal, and RF quality 718 identifies the quality of the RF signal. An RF test is useful in identifying paired infusion pumps infusion pump 300, and in troubleshooting the RF communication between remote controller 200 and infusion pump 300. When using more than one remote controller 200 with a single infusion pump 300, the RF test can also be helpful in displaying pairing specifics to the user.

Figure 14:
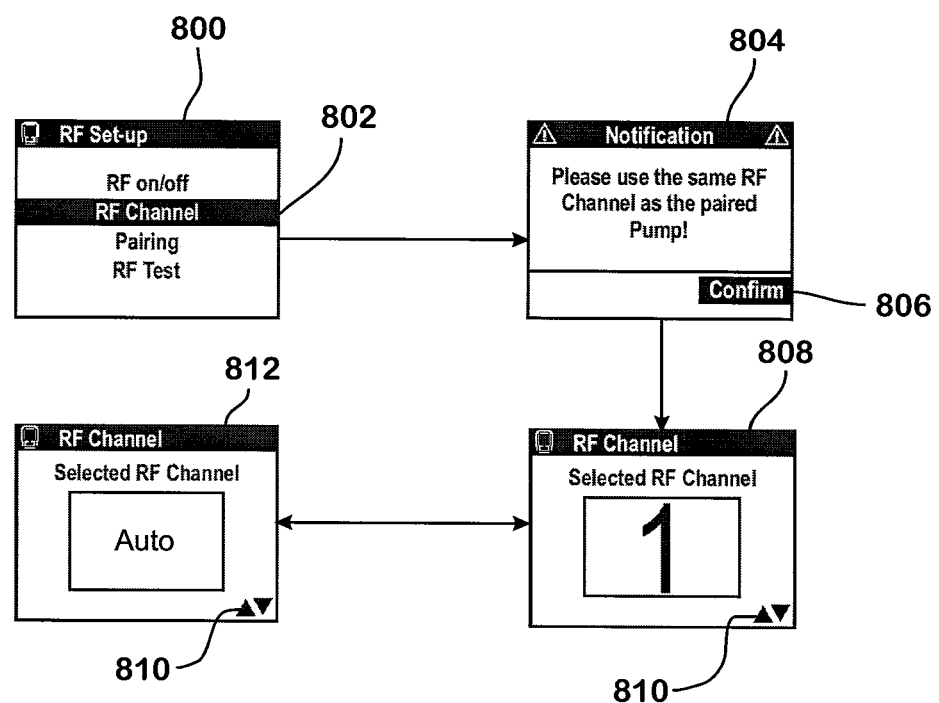
FIG. 14 illustrates RF communication setup screens that may be displayed on the remote controller in one exemplary embodiment.
Figure 15:
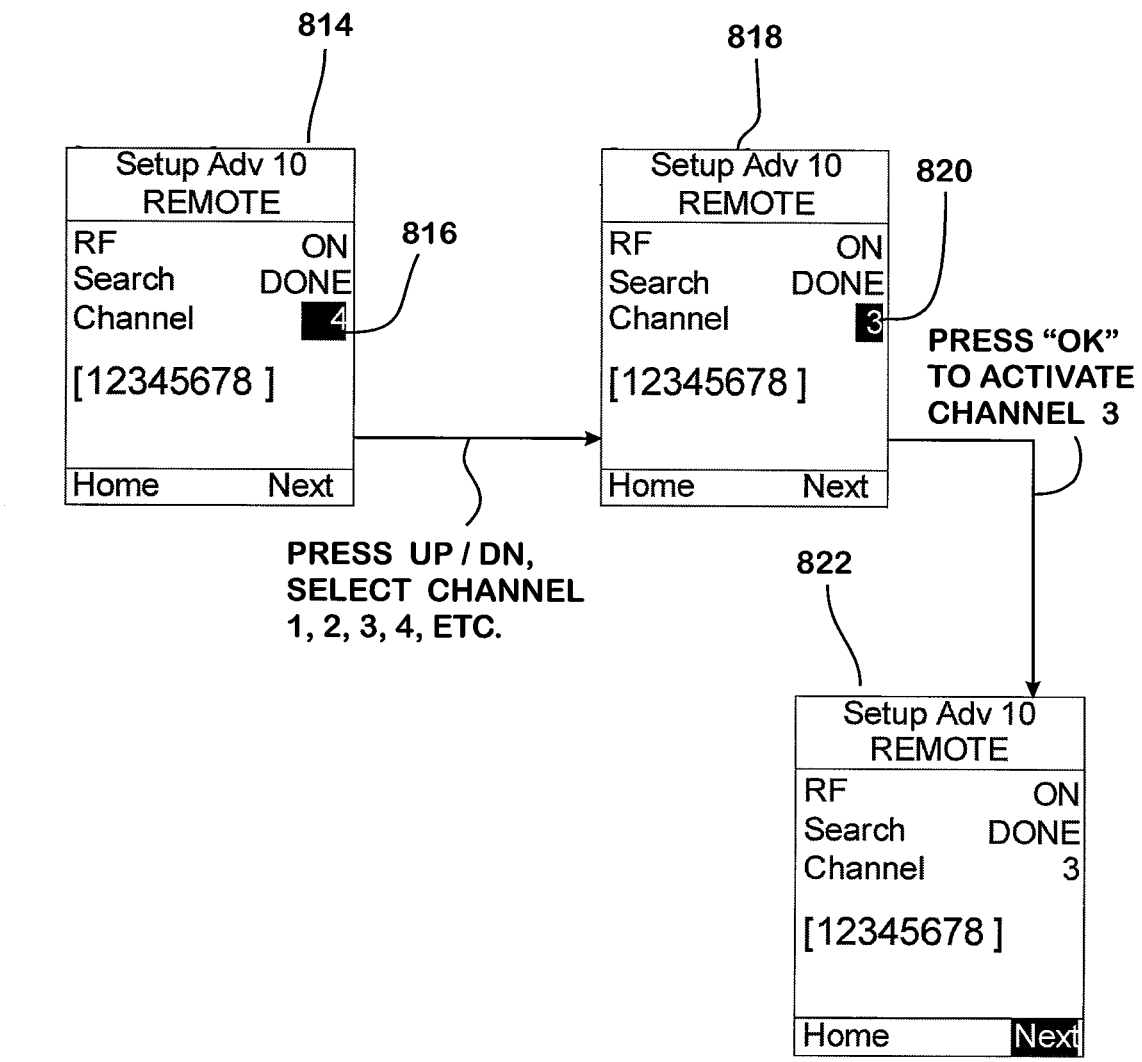
FIG. 15 illustrates RF communication setup screens that may be displayed on the medical device in one exemplary embodiment.
Figure 25:
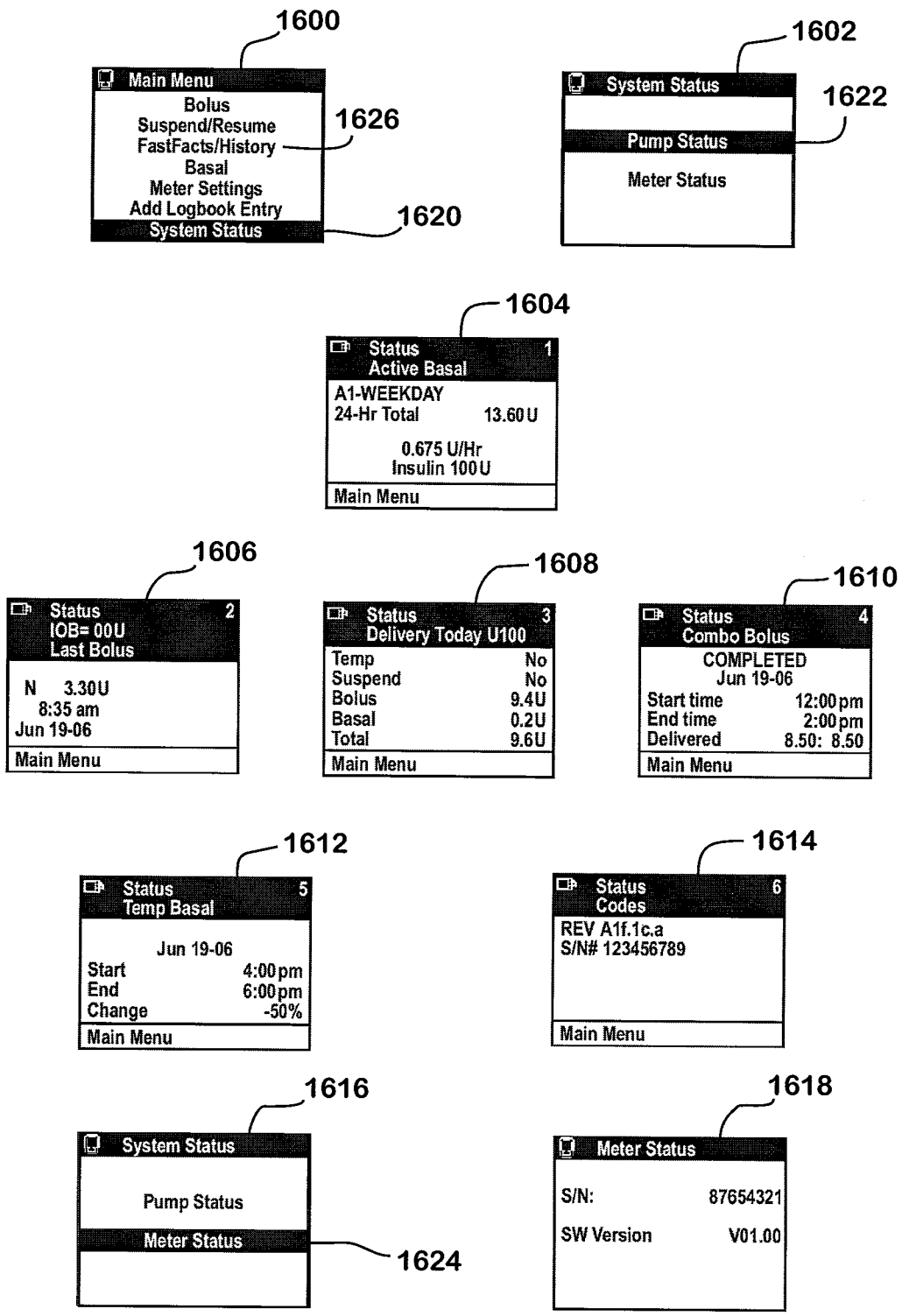
FIG. 25 illustrates a series of medical device and remote controller status screens that may be displayed on the remote controller in one exemplary embodiment.

FIGS. 14 and 15 illustrate RF communication setup screens that may be displayed on remote controller 200 and infusion pump 300, as used in the exemplary embodiments. FIG. 14 illustrates RF setup screen 800, which is displayed on remote controller 200. When RF channel 802 is highlighted and selected, RF channel selection screens are displayed. In notification 804, the user is notified that the same RF channel should be used on both remote controller 200 and infusion pump 300, and must confirm the notification using confirm 806. Depending on RF channel settings, either RF channel screen 808 or RF channel screen 812 is displayed, with toggle icon 810 indicating that RF channel screen 808 can be toggled through several channels, or can be toggled to RF channel screen 812 for automatic RF channel selection. Screen 808, with manual selection of the appropriate channels is utilized in the preferred embodiments. FIG. 25 illustrates a series of user interface screens that are displayed on infusion pump 300 and allow a user to either automatically select an RF channel, or to specify an RF channel manually. In remote setup screen 814, the current RF channel is highlighted, as illustrated by channel 816. Using second up button 304 and/or second down button 310, a different channel number can be selected, as illustrated by channel 820 in remote setup screen 818, or the channel selection can be set to automatic. Once the desired channel has been highlighted, second OK button 314 is pressed to program infusion pump 300 to that channel, and remote setup screen 822 is displayed.

Figure 16A:
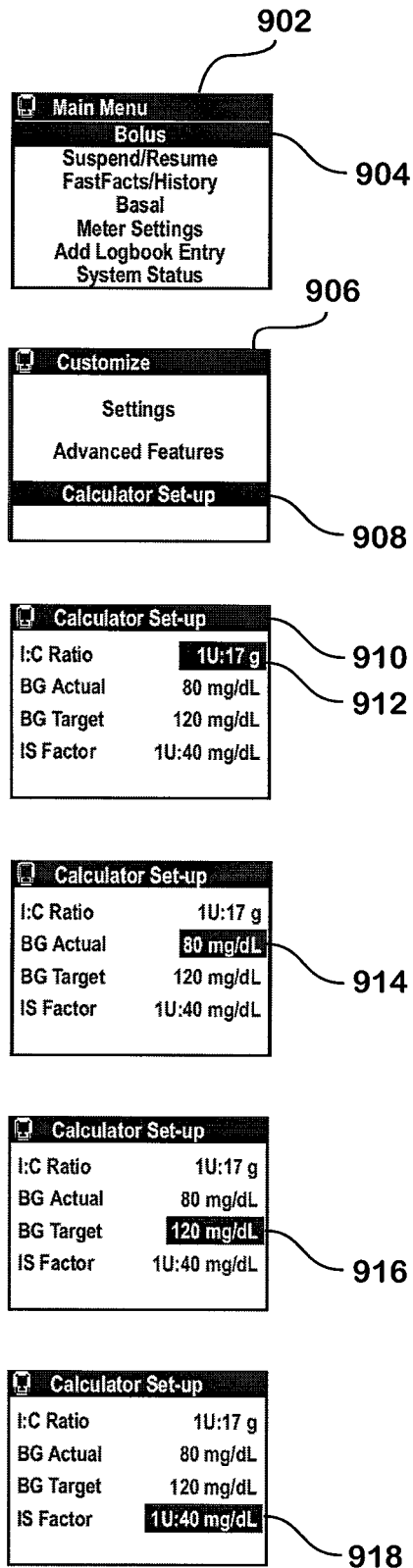
FIGS. 16A and 16B illustrate bolus calculator setup screens that may be displayed on the remote controller in one exemplary embodiment.
Figure 16B:
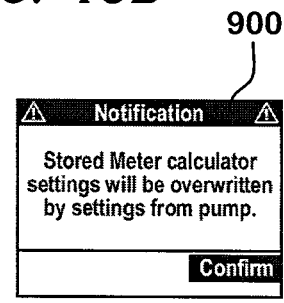

FIGS. 16A and 16B illustrate bolus calculator setup screens that may be displayed on the remote controller, as used in the exemplary embodiments. The screens illustrated in FIG. 16A are used when remote controller 200 is not paired with infusion pump 300. When remote controller 200 is paired with infusion pump 300, calculator settings are automatically copied from infusion pump 300 to remote controller 200. As illustrated in FIG. 26B, when pairing remote controller 200 to infusion pump 300, notification 900 is displayed to the user on remote controller 200, reminding the user that values stored in remote controller 200 will be overwritten with those stored in infusion pump 300 when pairing between remote controller 200 and infusion pump 300 is confirmed by the user. When remote controller 200 is used only and only as a stand-alone device without being paired with infusion pump 300, bolus calculations can be performed by remote controller 200 using calculator settings entered by the screens illustrated in FIG. 16A. In main menu screen 902, bolus 904 is highlighted and selected, leading to customize screen 906. In customize screen 906, calculator setup 908 is highlighted and selected, leading to calculator setup screen 910. In calculator setup screen 910, various bolus calculator settings can be made, including I:C Ratio 912, BG Target 916, BG Delta xxx and IS Factor 918. I:C Ratio 912, BG Target 916, BG Delta xxx and IS Factor 918 are used in calculating various types of bolus delivery, including those that will compensate for carbohydrate intake and those that will return blood glucose values to desired levels. I:C Ratio 912 is used to set an insulin to carbohydrate ratio, and is used in calculating a bolus that will compensate for ingestion of carbohydrates from a meal or snack. It is defined as the approximate number of grams of carbohydrates that can be compensated with one unit of insulin. BG Target 916 allows the user to enter a target blood glucose value. Target blood glucose values are used when maintaining good glycemic control. Although not specifically illustrated, BG Delta xxx allows the user to enter a value that is added to and subtracted from the BG Target 916 in order to define an acceptable range of blood glucose values for the user. If the user's current blood glucose reading is within the range then the meter will not adjust its insulin recommendation to compensate for the blood glucose reading being above or below BG Target 916.

Among computations made by the remote controller 200 and the infusion pump 300 are, for example, suitable bolus delivery recommendations. In a normal delivery, the entire insulin bolus is delivered all at once. With a combo bolus delivery, the user can select a percentage of the infusion to deliver at once, termed the "normal" portion, with the remaining percentage, termed the "extended" portion, delivered over an extended period of time as set by the user. The user can select the initial delivery amount from 0% to 100% thereby allowing an all extended delivery and all normal delivery respectively. A BG combo delivery works like the combo bolus delivery except that the insulin needed for BG correction is added to the normal portion of the delivery.

Each of the devices preferably uses two calculations to provide for the recommended bolus delivery: "ezBG" and "CarbSmart." The ezBG computation does not account for carbohydrates while the CarbSmart calculation includes carbohydrates. The microprocessor of either the remote controller or the infusion pump can perform the ezBG bolus computation. The preferred equation for ezBG Bolus Total is:

$$\text{ezBG Bolus Total}=((\text{BGM}-\text{TargetBG})/\text{ISF})-\text{IOB}, \text{ and}$$
$$\text{ezBG Bolus Total is not negative.}$$

Where:
BGM=blood glucose measurement
TargetBG=target blood glucose setting at the current time with a +/− range or user entered target (where BG correction is zero if the measurement is within tolerance)
ISF=insulin sensitivity factor setting at the current time or user entered factor
IOB=calculated Insulin on Board based on the insulin delivered but not yet absorbed by the body or zero if the IOB feature is disabled. The curve used to determine the IOB can be an approximation of the Novolog and Humalog fast-acting insulin absorption curves The preferred equations for CarbSmart Bolus Total can be determined depending on several factors relating to blood glucose measurements:
In the event that BG>=0 and BG>IOB, CarbSmart Bolus Total=Carb+(BG−IOB);
In the event that BG>=0 and (BG−IOB)<0, CarbSmart Bolus Total=Carb; and
In the event that BG<0, CarbSmart Bolus Total=Carb+(BG−IOB) and CarbSmart Bolus Total is negative
Where:
BG=(BGM−TargetBG)/ISF
Carb=entered carbohydrates/I:C
IOB=calculated Insulin on Board based on the insulin delivered but not yet absorbed by the body or zero if the IOB feature is disabled. The curve used to determine the IOB is an approximation of the Novolog and Humalog fast-acting insulin absorption curves BGM=blood glucose measurement
TargetBG=target blood glucose setting at the current time with a +/− range or user entered target
ISF=insulin sensitivity factor setting at the current time or user entered factor
I:C=insulin to carbohydrate ratio setting at the current time or user entered ratio.

Users have the option of delivering the recommended CarbSmart Bolus Total as a normal, combo or BG combo delivery. Combo deliveries allow the user to specify a percentage of the bolus for immediate delivery with the remainder delivered within the user specified duration. It should be noted that the BG can be calculated by the remote controller 200 using blood glucose measurement data stored or obtained in the remote controller 200 and transmitted to the device 300.

Figure 17:
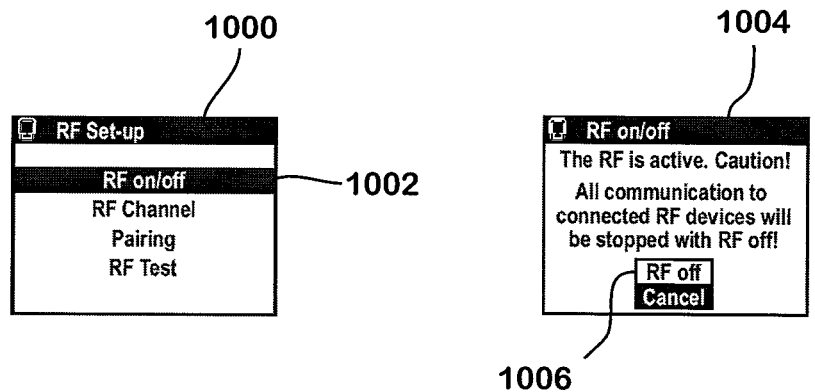
FIG. 17 illustrates RF communication on/off setup screens that may be displayed on the remote controller in one exemplary embodiment.
Figure 18:
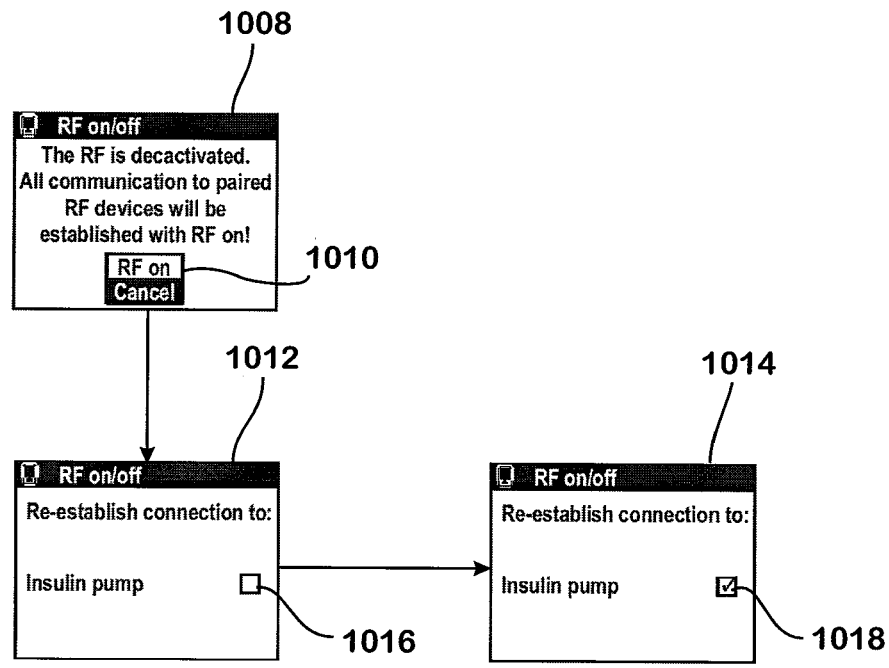
FIG. 18 illustrates screens for turning RF communication on that may be displayed on the remote controller in one exemplary embodiment.
Figure 27:
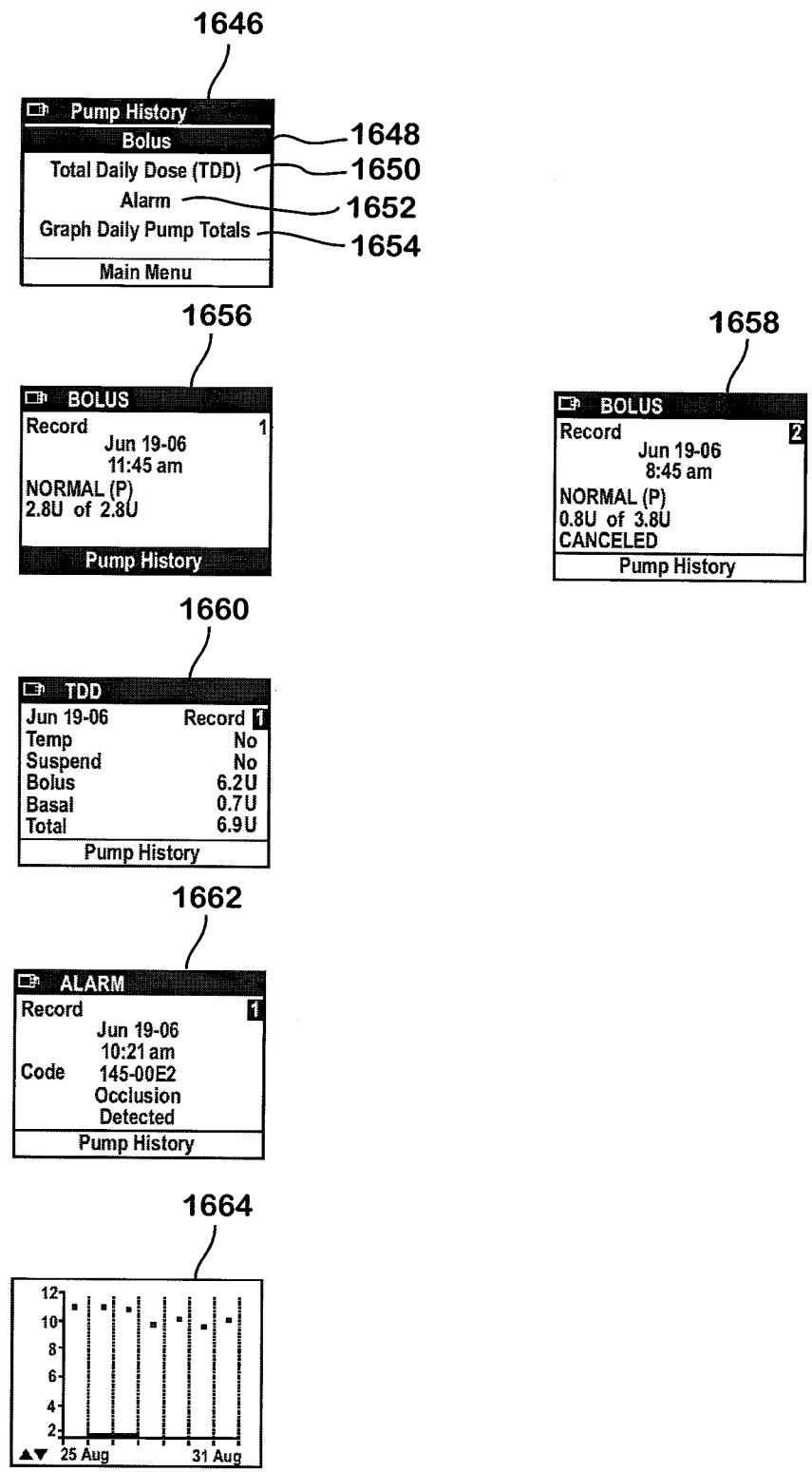
FIG. 27 illustrates a series of medical device history screens that may be displayed on the remote controller in one exemplary embodiment.

FIGS. 17 and 18 illustrate screens for turning RF communications on and off, and may be displayed on remote controller 200, as used in the exemplary embodiments. In FIG. 27, RF setup screen RF setup screen 1000 allows the user to select from among several RF setup options. By highlighting and selecting RF on/off 1002 a user can toggle RF communication on and off. In RF on/off screen 1004, the user is warned that communication between remote controller 200 and infusion pump 300 will stop when RF is turned off, and is prompted to continue turning RF off, or to cancel the command. If the RF is already turned off, the user will be warned that communication between paired devices will be reestablished if RF is turned on, as illustrated in RF on/off screen 1008 and RF on 1010 of FIG. 28. Once RF on 1010 has been selected, RF on/off screen 1012 is displayed, indicating that RF communication is being reestablished with the previously paired device connection status 1016. Once RF has been reestablished, it's indicated to the user by RF on/off screen 1014 and connection status 1018.

Figure 19:
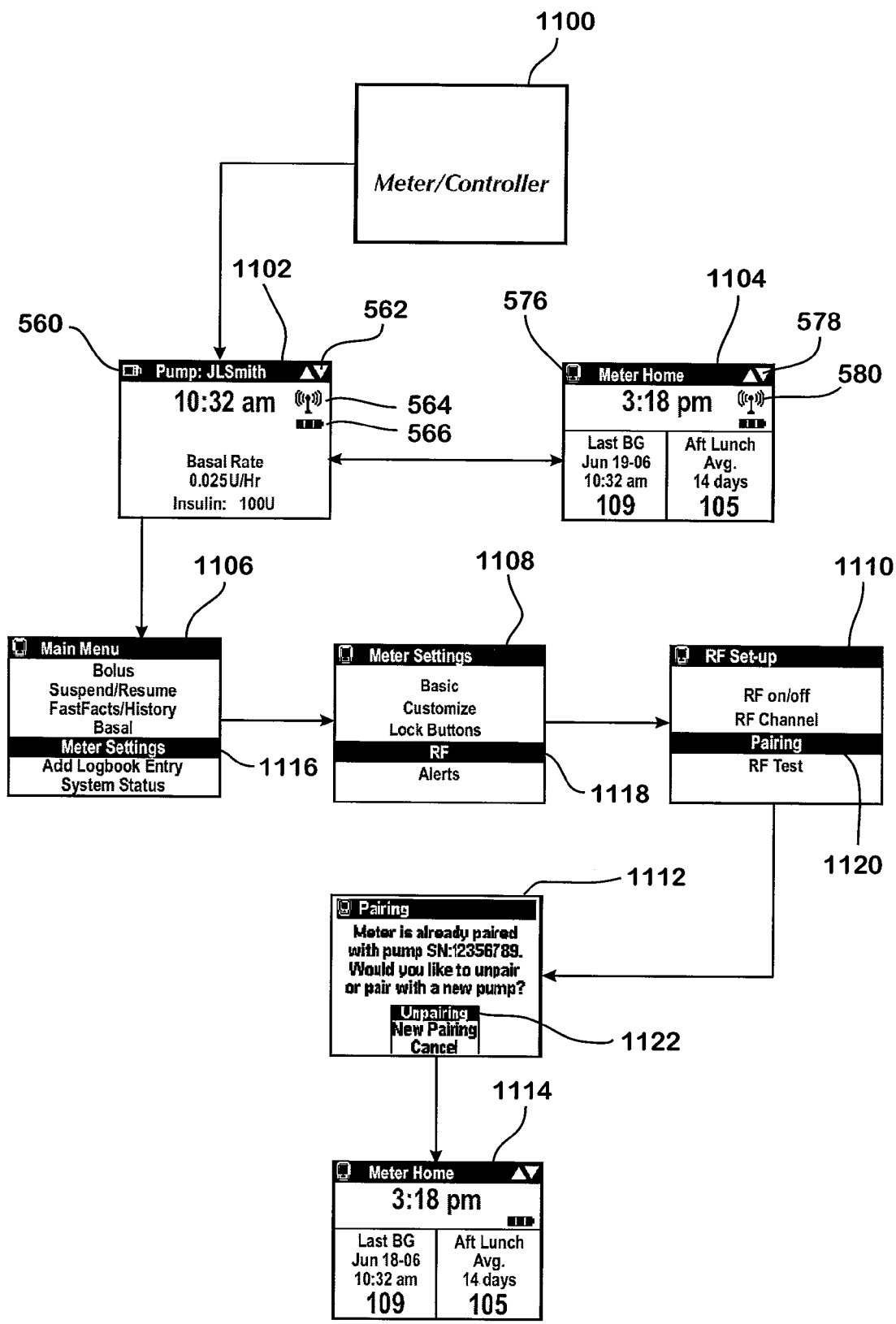
FIG. 19 is a flow chart illustrating screens for unpairing a remote controller and medical device that may be displayed on the remote controller in one exemplary embodiment.
Figure 20:
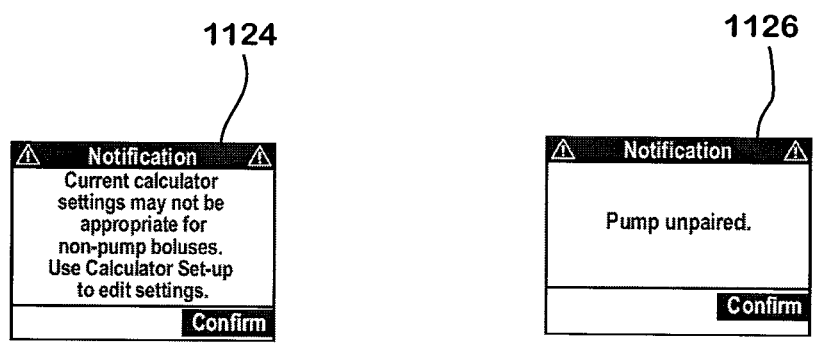
FIG. 20 illustrates notification screens that may be displayed on the remote controller during unpairing of a remote controller and medical device in one exemplary embodiment.

FIG. 19 is a flow chart illustrating screens for unpairing a remote controller and infusion pump that may be displayed on the remote controller, as used in the exemplary embodiments. When remote controller 200 is turned on, it displays splash screen 1100, followed by remote infusion pump home screen 1102. Remote infusion pump home screen 1102 is displayed because remote controller 200 is paired with infusion pump 300. Remote infusion pump home screen 1102 includes infusion pump icon 560, toggle icon 562, signal strength icon 564, and battery icon 566, as described previously. Infusion pump icon 560 indicates that remote infusion pump home screen 1102 is related to infusion pump 300 functions, and toggle icon 562 indicates that remote infusion pump home screen 1102 can be toggled with meter home screen 1104 by pressing first down button 206 and first up button 210. Meter home screen 1104 includes meter icon 576, toggle icon 578, and signal strength icon 580. Meter icon 576 indicates that meter home screen 1104 is related to remote controller 200 functions, while toggle icon 578 and signal strength icon 580 function as described previously. By pressing first OK button 204 while remote infusion pump home screen 1102 or meter home screen 1104 is displayed, main menu screen 1106 will be displayed. Highlighting and selecting meter settings 1116 causes meter settings screen 1108 to be displayed. Highlighting and selecting RF 1118 causes RF setup screen 1110 to be displayed, while highlighting and selecting pairing 1120 leads to pairing screen 1112. Pairing screen 1112 notifies the user that remote controller 200 is paired with infusion pump 300 (identified by serial number, or other identifying information as described previously), and allows the user to confirm unpairing by selecting unpairing 1122. After selecting unpairing 1122, meter home screen 1114 is displayed, without toggle icon 578 and signal strength icon 580, as were seen in meter home screen 1104. Toggle icon 578 and signal strength icon 580 are not displayed in meter home screen 1114 because remote controller 200 is no longer paired with infusion pump 300, remote infusion pump home screen 1102 is no longer an option for display, and RF is deactivated. When remote controller 200 and infusion pump 300 have been unpaired, various warning and notification screens can be displayed, such as notification 1124 and notification 1126, illustrated in FIG. 30.

Figure 21:
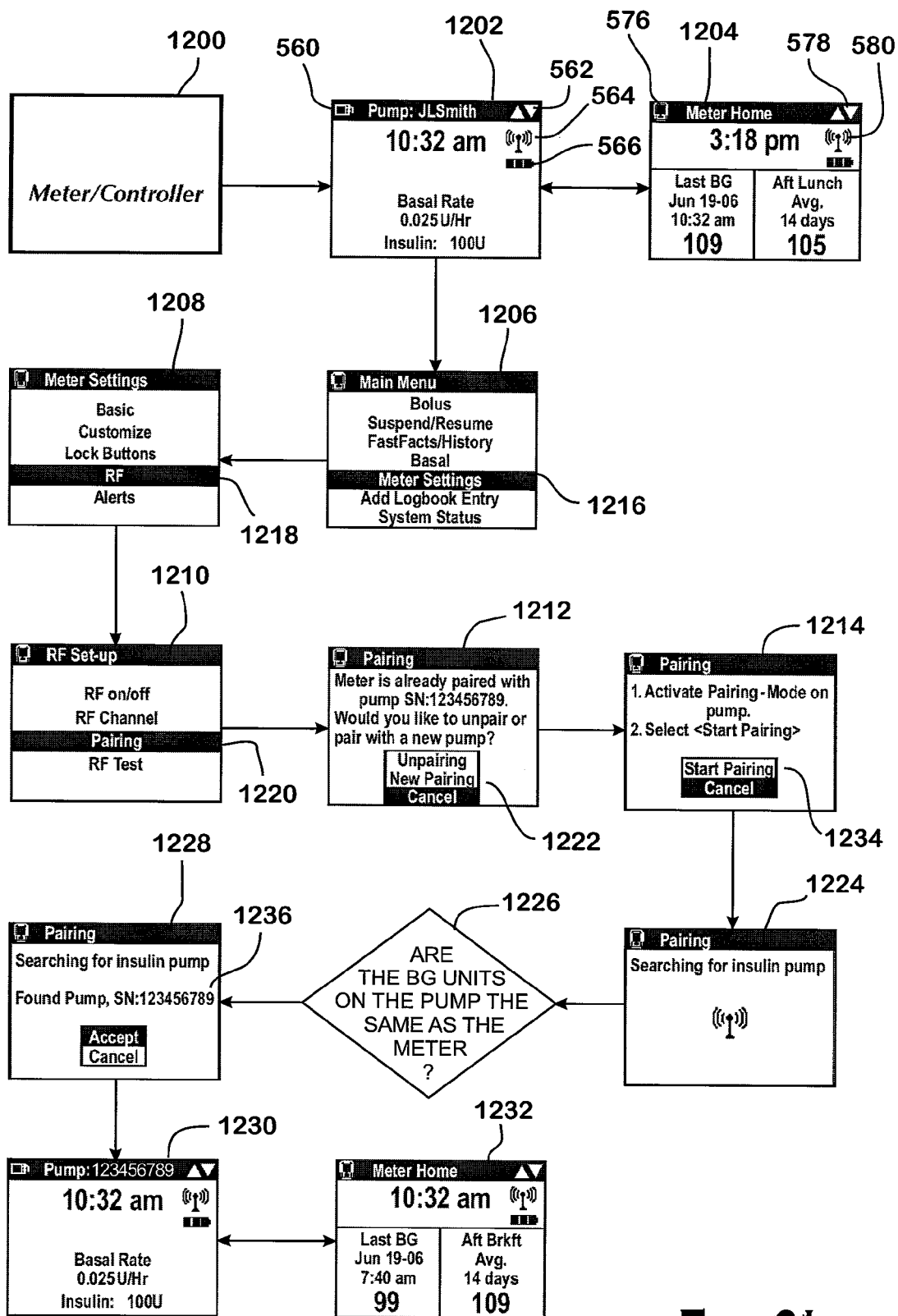
FIG. 21 is a flow chart illustrating screens for a new pairing of a remote controller and medical device that may be displayed on the remote controller in one exemplary embodiment.

FIG. 21 is a flow chart illustrating screens for a new pairing of remote controller 200 and infusion pump 300 that may be displayed on remote controller 200, as used in the exemplary embodiments. When remote controller 200 is turned on, it displays splash screen 1200, followed by remote infusion pump home screen 1202. Remote infusion pump home screen 1202 is displayed because remote controller 200 is paired with infusion pump 300. Remote infusion pump home screen 1202 includes infusion pump icon 560, toggle icon 562, signal strength icon 564, and battery icon 566, as described previously. Infusion pump icon 560 indicates that remote infusion pump home screen 1202 is related to infusion pump 300 functions, and toggle icon 562 indicates that remote infusion pump home screen 1202 can be toggled with meter home screen 1204 by pressing first down button 206 and first up button 210. Meter home screen 1204 includes meter icon 576, toggle icon 578, and signal strength icon 580. Meter icon 576 indicates that meter home screen 1204 is related to remote controller 200 functions, while toggle icon 578 and signal strength icon 580 function as described previously. By pressing first OK button 204 while remote infusion pump home screen 1202 or meter home screen 1204 is displayed, main menu screen 1206 will be displayed. Highlighting and selecting meter settings 1216 causes meter settings screen 1208 to be displayed. Highlighting and selecting RF 1218 causes RF setup screen 1210 to be displayed, while highlighting and selecting pairing 1220 leads to pairing screen 1212. Pairing screen 1212 notifies the user that remote controller 200 is paired with infusion pump 300 (identified by serial number, or other identifying information as described previously), and allows the user to confirm new pairing by selecting new pairing 1222. After selecting new pairing 1222, pairing screen 1214 is displayed, instructing the user to activate pairing mode on infusion pump 300, and to select start pairing 1234. Pairing screen 1224 is then displayed, indicating that remote controller 200 is searching for a new infusion pump 300. One parameter that is checked during the pairing search is that remote controller 200 and infusion pump 300 have the same glucose units of measure, as mentioned previously. If remote controller 200 and infusion pump 300 do not have the same glucose units of measure, the new pairing process is aborted. Assuming that the same units of measure are found, pairing screen 1228 is then displayed, indicating that a new infusion pump 300 has been found, and including identification 1236 and any other identifying information, as described previously. After accepting the pairing, remote infusion pump home screen 1230 is displayed. Remote infusion pump home screen 1230 includes identifying information for new infusion pump 300, and can be toggled with meter home screen 1232 using first down button 206 and first up button 210.

Figure 22:
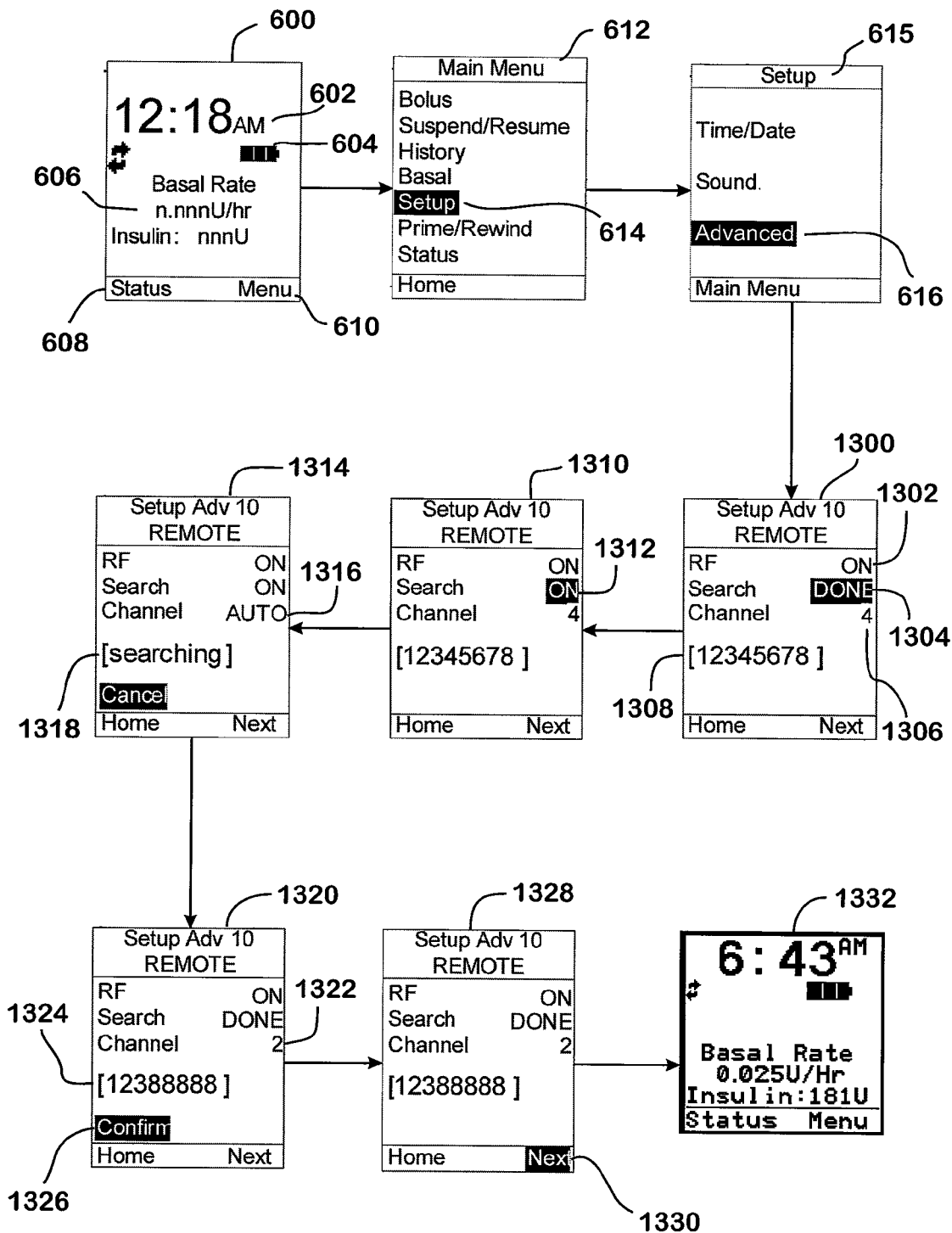
FIG. 22 is a flow chart illustrating screens for a new pairing of a remote controller and medical device that may be displayed on the medical device in one exemplary embodiment.

FIG. 22 is a flow chart illustrating screens for a new pairing of remote controller 200 and infusion pump 300 that may be displayed on the infusion pump, as used in the exemplary embodiments. When infusion pump 300 is turned on, local infusion pump home screen 600 is displayed. Local infusion pump home screen 600 includes time 602, battery icon 604, delivery status 606, status command 608, and menu command 610, described previously in reference to FIG. 7. After highlighting menu command 610 using second up button 304 and second down button 310, second OK button 314 is pressed and main menu screen 612 is displayed. Second up button 304 and second down button 310 can be used to highlight setup 614 and second OK button 314 is pressed to display setup screen 615. After highlighting and selecting advanced 616, remote setup screen 1300 is displayed. Remote setup screen 1300 includes RF 1302, search 1304, channel 1306, and identification 1308. Since infusion pump 300 is already paired to a remote controller 200, RF 1302 is ON, search 1304 indicates DONE, and channel 1306 is set to a channel over which RF communication between remote controller 200 and infusion pump 300 occurs. Identification 1308 displays identifying information as to the paired remote controller 200. In remote setup screen 1310, search 1312 has been switched to ON, initiating a new pairing search. Remote setup screen 1314 displays the ongoing search status, where channel 1316 has automatically been set to AUTO since a new search is under way, and search status 1318 indicates that infusion pump 300 is searching for a new remote controller 200. Once a new remote controller 200 has been found, remote setup screen 1320 is displayed. Channel 1322 is set to the new channel for RF communication that was automatically set by 328, and identification 1324 displays new identifying information for remote controller 200. Confirm 1326 prompts the user to confirm pairing with new remote controller 200. Once new pairing is confirmed, remote setup screen 1328 is displayed. Selecting next 1330 completes the new pairing process, and returns the display to local infusion pump home screen 1332.

In alternative embodiments, multiple remote controllers 200 can be paired with a single infusion pump 300. This allows a user to have backup remote controllers 200, or allows them to keep remote controllers 200 in multiple locations, such as at home and at the office. Each remote controller 200 must initially be paired with infusion pump 300 to exchange identifying information. An RF detection algorithm in infusion pump 300 determines if it is possible to transfer remote control from one remote controller 200 to another. In addition, an acknowledgment from the user is required when switching remote control from one remote controller to another. As mentioned previously, each remote controller 200 must be initially paired with infusion pump 300. Pairing information for each remote controller 200 is stored in non-volatile memory within infusion pump 300. Pairing information can be stored for several remote controllers 200. Pairing information may include an RF address which is unique and assigned by the device manufacturer, an RF type which identifies the type of device being paired, a default channel which specifies the channel over which communication will occur the next time communications are established, flags that include additional information such as hardware/software revision levels and units of measure, and serial numbers that uniquely identify each remote controller 200. An algorithm in infusion pump 300 determines when remote controller 200 may be changed. While 200 and 300 are paired, and are in RF communication with each other, they routinely communicate. For instance, on a regular interval, remote controller 200 requests the status of 300 by way of RF communication. If infusion pump 300 does not communicate with the currently paired remote controller 200 within a fixed time, it will start to search for previously paired, and memorized, remote controllers 200. For efficiency, the search starts with the most recently paired remote controller 200. The dwell time spent searching for each previously paired controller is based on the minimum system RF sniff time. Once a previously paired remote controller 200 is found, the user is prompted to acknowledge transfer of remote control to the previously paired remote controller 200. An advantage of this embodiment is that it is easier for the user to switch between previously paired devices.

Figure 23:
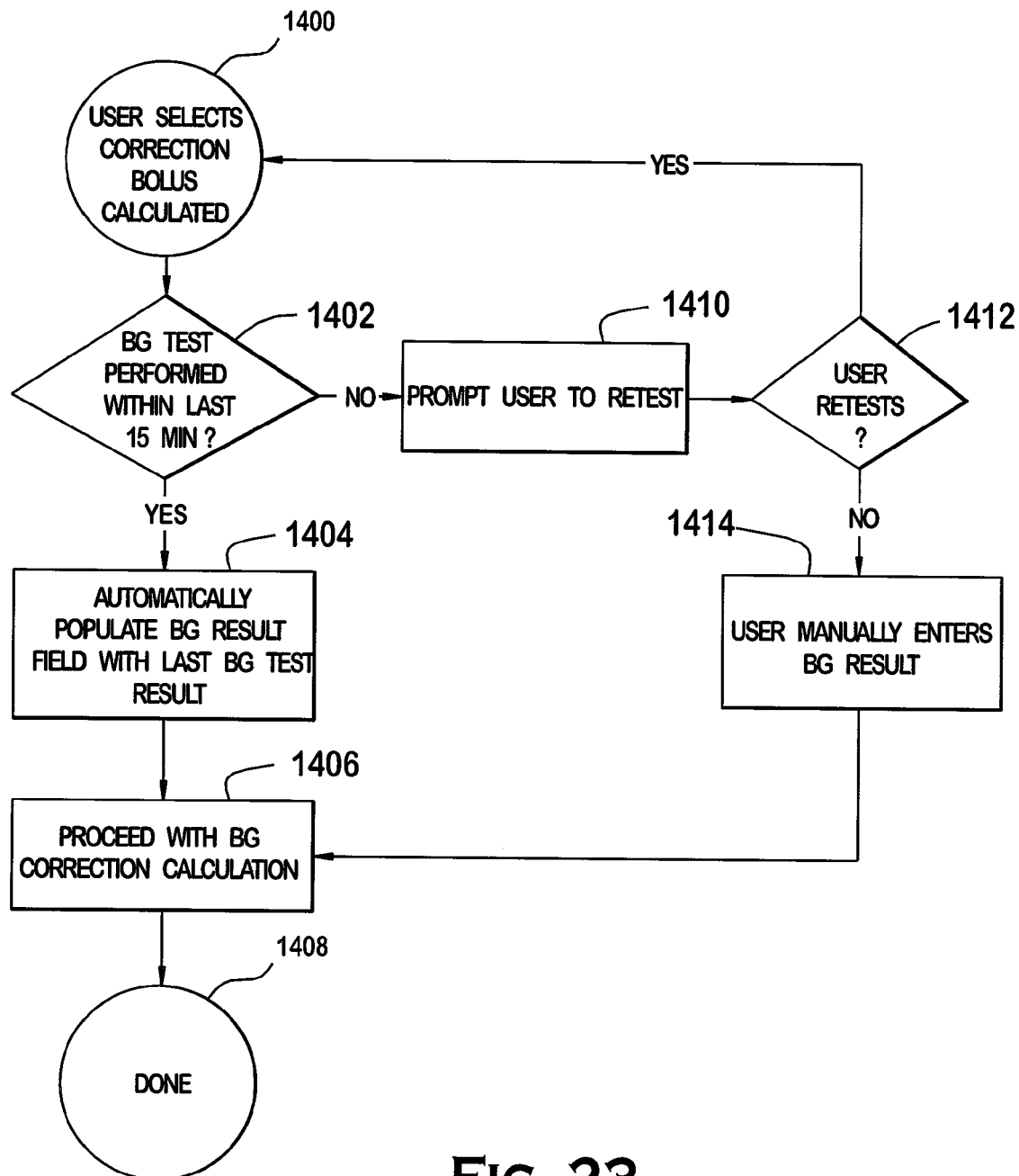
FIG. 23 is a schematic flow chart that illustrates a method of establishing an acceptable time window for blood glucose results measured by a remote controller and relied upon in bolus calculations in one exemplary embodiment.

FIG. 23 is a schematic flow chart that illustrates a method of establishing an acceptable time window for blood glucose results measured by a remote controller and relied upon in bolus calculations, as used in the exemplary embodiments. The method illustrated in FIG. 23 can be used in remote controller 200 or in infusion pump 300. The process begins by in initiating step 1400. Step 1400 can be initiated immediately after measuring blood glucose with remote controller 200, or can be initiated after measuring blood glucose with a separate blood glucose meter. Step 1400 can be initiated whenever the user would like to deliver a bolus. Once step 1400 is initiated, memory in remote controller 200 or infusion pump 300 is checked for recent blood glucose measurements. In a particularly preferred embodiment, recent blood glucose measurements are those taken within the last 15 minutes. If a blood glucose measurement was taken within the last 15 minutes, it is automatically entered into the bolus calculator, as illustrated in step 1404. Using the recent blood glucose measurement and the calculator settings (discussed previously), a recommended bolus is calculated, as illustrated in step 1406. Once a bolus amount has been recommended, the bolus calculation is done, as illustrated by step 1408, and the user has the choice of making adjustments to or delivering the recommended bolus.

In the preferred embodiments, BG results are only entered on the pump 300 when a bolus calculation is done on the pump 300. That result must be manually entered by the user into the pump 300. Such result stored in pump 300 is then transferred to the memory of controller 200 during the next communication interval.

In situations where a recent blood glucose value is not available, the user is prompted to retest their blood glucose, as illustrated in step 1410. If they choose to retest using remote controller 200, they return to step 1400 of the process, and the result is automatically transferred to the bolus calculator as in step 1404. If they choose not to retest, or if they retest using a separate blood glucose meter, the user can manually enter a blood glucose result, as illustrated in step 1414. As soon as the user manually enters a blood glucose value, the blood glucose calculator determines a recommended bolus, as in step 1406, and the user has the choice to adjust or deliver the recommended bolus. In situations where the blood glucose value is measured with remote controller 200 and sent to infusion pump 300 for use in bolus calculations, it is particularly important that the time setting of both remote controller 200 and infusion pump 300 are the same. If the time setting of remote controller 200 and infusion pump 300 are not the same, it is impossible to accurately determine the age of a blood glucose reading.

Figure 24:
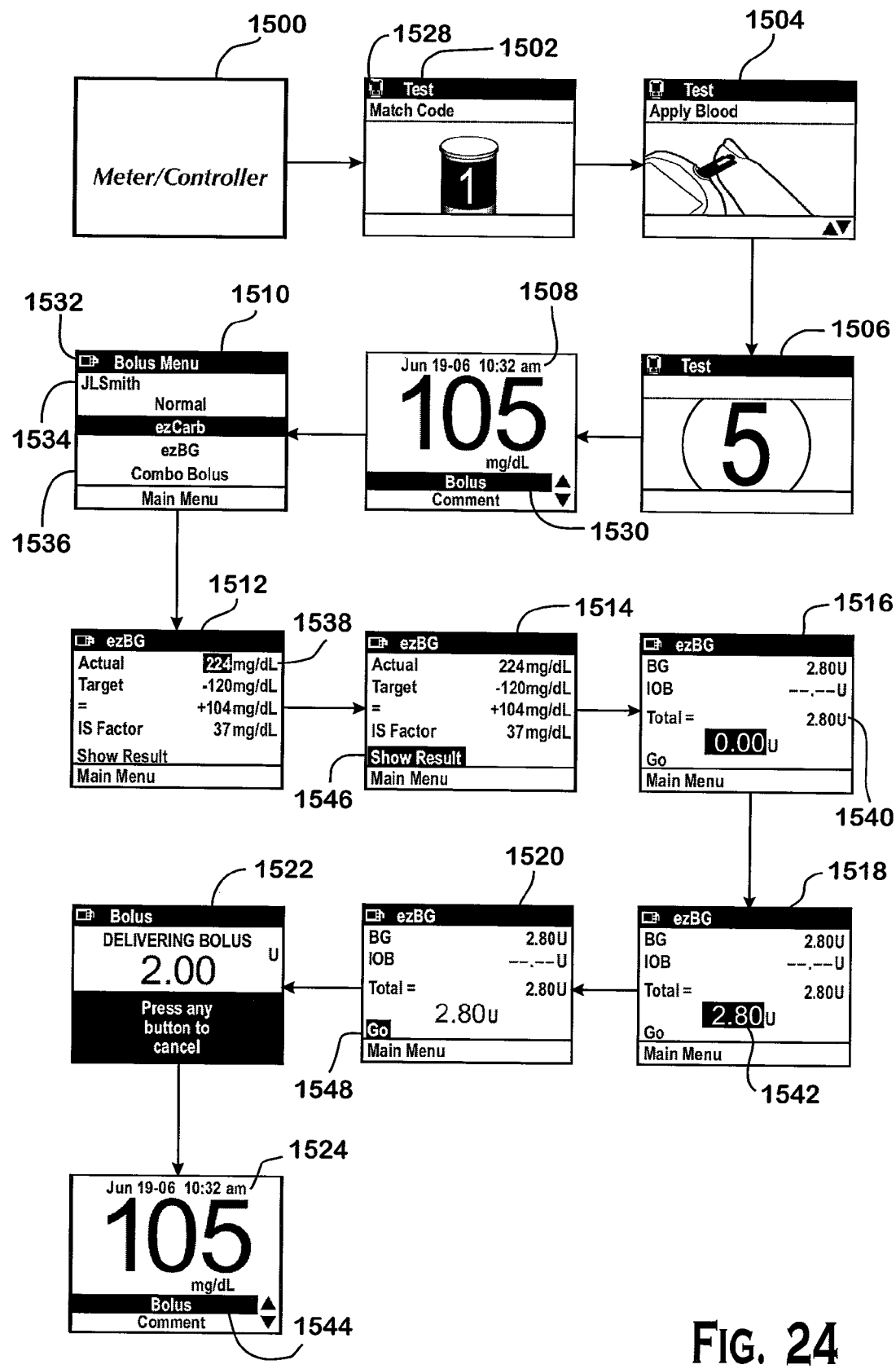
FIG. 24 is a flow chart illustrating screens for calculating and delivering a bolus, that may be displayed on the remote controller in one exemplary embodiment.

FIG. 24 is a flow chart illustrating screens for calculating and delivering a bolus, that may be displayed on remote controller 200, as used in the exemplary embodiments. Upon inserting a test strip into remote controller 200, splash screen 1500 is displayed, followed by test screen 1502. Test screen 1502 includes meter icon 1528, indicating that it is a display screen related to remote controller functions. Test screen 1502 indicates to the user that they should check that the lot code on their test strips matches the lot code entered in remote controller 200. The user is then prompted to apply blood to the test strip, after which test screen 1506 appears, counting down to a result. Upon completion of the blood glucose test, the blood glucose concentration is displayed using result screen 1508. Included in result screen 1508 is bolus 1530, which leads to bolus menu screen 1510 when selected. Bolus menu screen 1510 includes infusion pump icon 1532, identification 1534, and ezBG 1536. Infusion pump icon 1532 indicates that bolus menu screen 1510 is related to infusion pump functions, identification 1534 includes identifying information (such as infusion pump serial number or a familiar name), and ezBG 1536 accesses a bolus calculator that allows correction for high blood glucose concentrations. Upon selecting ezBG 1536, ezBG calculator screen 1512 is displayed. As long as a blood glucose reading has been made with remote controller 200 within the last 15 minutes, actual BG 1538 includes a value for actual blood glucose. If a reading has not been made by remote controller 200 within the last 15 minutes, the field contains a default value (obtained from the infusion pump 300), which can be changed by the user. Once an actual blood glucose value has been set (either automatically, or by the user), ezBG calculator screen 1514 is displayed. After selecting show result 1546, ezBG total screen 1516 is displayed. ezBG total screen 1516 includes recommended bolus 1540, a recommended bolus amount that is based upon the data entered in ezBG calculator screen 1514. In screen ezBG total screen 1518, the user has an option to enter the recommended bolus amount 1540, or they can alter the user-entered bolus 1542. Once user entered bolus 1542 has been entered, ezBG total screen 1520 is displayed. By entering go command 1548, bolus delivery begins, as indicated in bolus screen 1522. Initiation of bolus delivery can be accompanied by visual or audio clues, such as beeps, tunes, or flashing lights. Upon completion of bolus delivery, result screen 1524 is displayed, where users can enter comments or return to home screens, as desired. Although FIG. 24 illustrates the use of a bolus calculator in respect to blood glucose correction boluses, a similar approach can be used when using bolus calculators to determine a bolus amount to compensate for carbohydrate intake. In cases where the bolus is used to compensate for carbohydrate intake, additional parameters are entered by the user, such as recent carbohydrate intake.

Figure 26A:
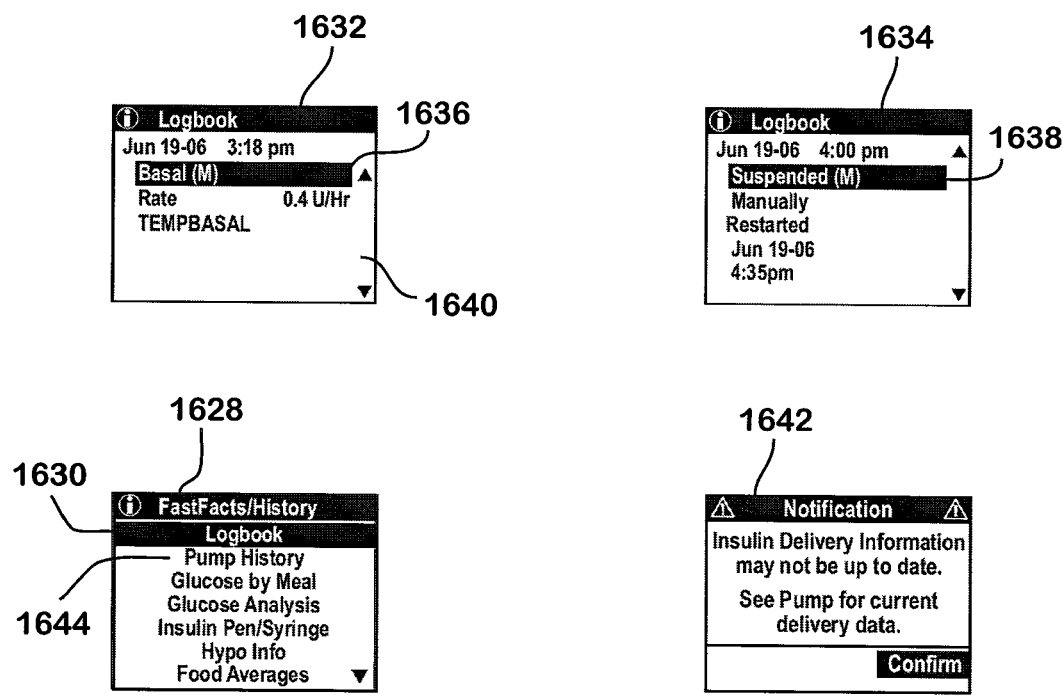
FIG. 26 illustrates a series of logbook and notification screens that may be displayed on the remote controller in one exemplary embodiment.
Figure 26B:
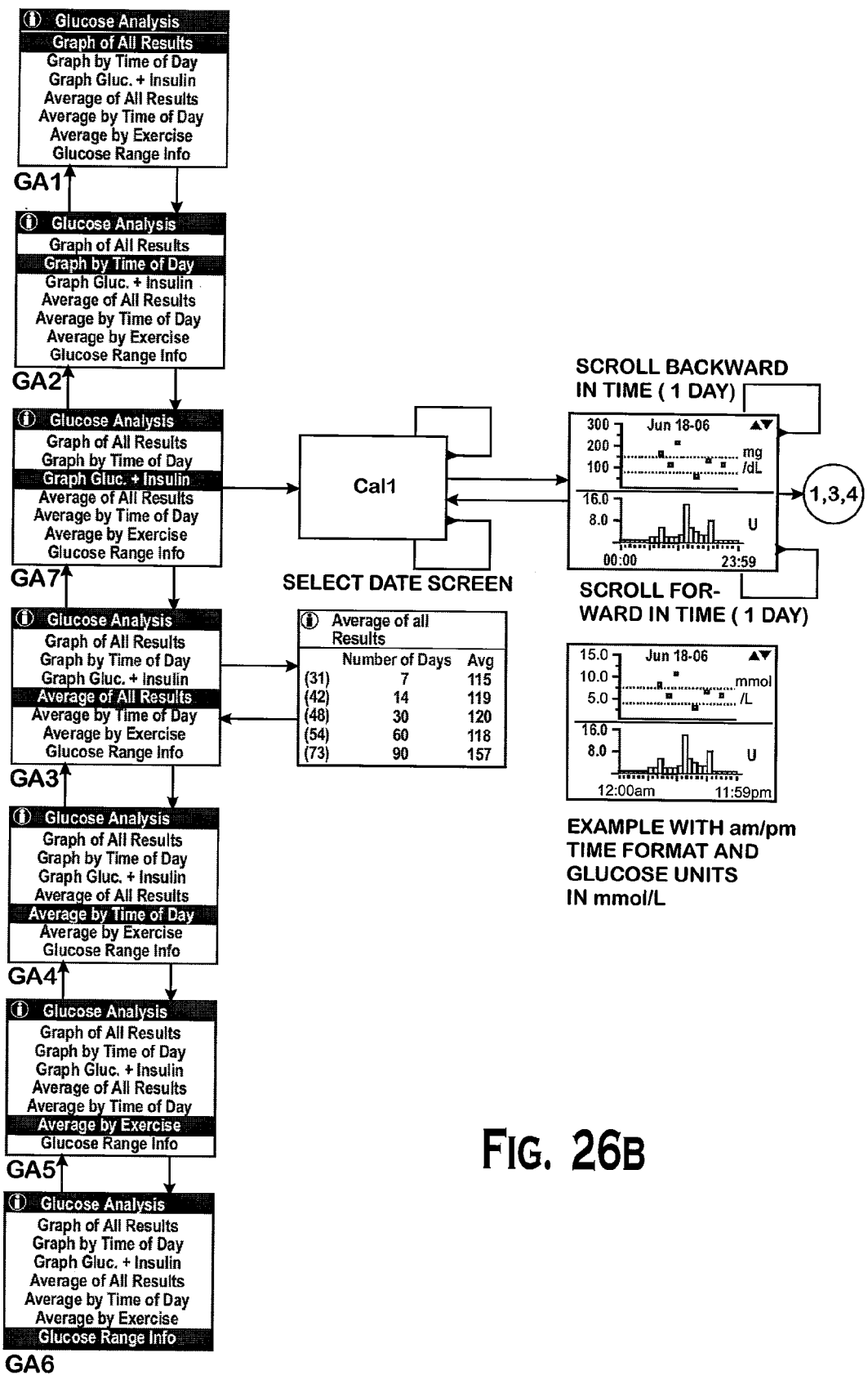

FIGS. 25, 26A, and 27 illustrate a series of screens displayed on remote controller 200 that relate to the status of infusion pump 300, the status of remote controller 200, the logbook of remote controller 200, and the history of infusion pump 300, as used in the exemplary embodiments. In FIG. 35, main menu screen 1600 includes submenu item system status 1620. When system status 1620 is selected, system status screen 1602 is displayed. Selecting infusion pump status 1622 results in display of active basal screen 1604, last bolus screen 1606, daily delivery screen 1608, combo bolus screen 1610, temporary basal screen 1612, and infusion pump codes screen 1614. Active basal screen 1604 displays basal delivery by infusion pump 300, last bolus screen 1606 displays bolus delivery by infusion pump 300, daily delivery screen 1608 displays total delivery by infusion pump 300 for the day, combo bolus screen 1610 displays the status of combination bolus delivery by infusion pump 300, temporary basal screen 1612 displays temporary basal delivery by infusion pump 300, and infusion pump codes screen 1614 displays identifying information related to infusion pump 300 such as software revision numbers and serial numbers. When system status screen 1616 is displayed, meter status 1624 can be selected, resulting in display of meter status screen 1618. Meter status screen 1618 includes identifying information related to remote controller 200, such as the serial number of remote controller 200 and its software revision number. If fast facts/history 1626 is selected while main menu screen 1600 is displayed, fast facts/history screen 1628 is displayed, as illustrated in FIG. 26A. Highlighting and selecting logbook 1630 results in the display of logbook entries such as logbook screen 1632 and logbook screen 1634. In logbook screen 1632, a record related to basal delivery by infusion pump 300 is displayed. Logbook screen 1632 includes an identifier (M), indicating that this particular basal delivery by infusion pump 300 was initiated by a command from remote controller 200. Scroll 1640 indicates that other logbook records can be accessed by pressing first down button 206 and first up button 210. By pressing first down button 206 or first up button 210, logbook screen 1634 is displayed. Logbook screen 1634 is a record of suspended delivery by infusion pump 300. Suspend record 1638 includes identifier (P) indicating that the command to suspend delivery by infusion pump 300 was initiated on infusion pump 300. Identifiers (M) and (P) illustrate a way to keep track of whether commands to infusion pump 300 were initiated by the user by way of remote controller 200 or if commands to infusion pump 300 were initiated by the user by way of infusion pump 300. This can help in diagnosing problems associated with use of remote controller 200 and infusion pump 300, and can not only be kept in user accessible areas such as a logbook, but can also be written into memory only accessible by the manufacturer of remote controller 200 and infusion pump 300. This type of memory is often referred to as a "black box", and can be used in diagnosing problems associated with operation of remote controller 200 or infusion pump 300. Although FIG. 26A illustrates record retention on remote controller 200, similar approaches can be used to store records directly on infusion pump 300. In fact, it is often beneficial to keep a copy of all records associated with operation of remote controller 200 and infusion pump 300 on both remote controller 200 and infusion pump 300. Hence, there can be an all-inclusive "black box" in both remote controller 200 and infusion pump 300. If RF communication between remote controller 200 and infusion pump 300 are not enabled when the logbook on remote controller 200 is accessed, the user is warned with notification 1642. Notification 1642 indicates that delivery data from infusion pump 300 may be out of date, and that the user should check logs in infusion pump 300 for up-to-date logbook records. Returning to fast facts/history screen 1628, if infusion pump history 1644 is selected, infusion pump history screen 1646 is displayed, as illustrated in FIG. 37. Infusion pump history screen 1646 includes bolus 1648, total daily dose 1650, alarm 1652, and graph daily infusion pump totals 1654. When bolus 1648 is selected, screens such as bolus screen 1656 and bolus screen 1658 are displayed. Bolus screen 1656 and bolus screen 1658 are examples of bolus delivery records, and may include information regarding command origination (M) or (P), time of bolus, type of bolus, amount of bolus, and degree of completion of bolus. When total daily dose 1650 is selected on infusion pump history screen 1646, records such as total daily dose screen 1660 are displayed. Total daily dose screen 1660 summarizes total daily delivery by infusion pump 300, and can include information regarding the date, the amount of temporary delivery, the number of suspended deliveries, the amount of bolus delivery, the amount of basal delivery, and the total delivery for that day. When alarm 1652 is selected on infusion pump history screen 1646, records such as alarm screen 1662 are displayed. Alarm screen 1662 includes alarm records for infusion pump 300, such as the time and date of the alarm, codes for the alarm, and a description of the alarm. Alarm records can also include identifying information to indicate if the alarm is a result of commands entered by the user using remote controller 200 or infusion pump 300. When graph daily infusion pump totals 1654 is selected when infusion pump history screen 1646 is displayed, screens such as graph 1664 are displayed, graphically illustrating daily delivery totals for infusion pump 300.

Referring to FIG. 26B, at least one of display of the remote controller 200 or infusion pump 300 can be utilized to display information relating to blood glucose measurements in a graphical format on a display screen, shown here in screens GA1-GA6. Under the "Fast Facts/History" screen of FIG. 26A, the Glucose Analysis screen can be selected to provide for menu screen GA1. Under GA1, analytical information are provided such as, for example, under screen GA1, a graph of all glucose measurement results stored in at least one of the remote controller and pump; under screen GA2, the information relating to blood glucose measurements include a graph of blood glucose measurement results as indexed by time of day; under screen GA7, the information include a graph of blood glucose measurements and insulin doses stored on at least one of the remote controller and infusion pump; under screen GA3, the information include an average of at least one of blood glucose measurements and insulin doses; under screen GA4 the information relating to blood glucose measurements comprise an average of at least one of blood glucose measurements and insulin doses indexed by time of day; under screen GA5, the information include an average of at least one of blood glucose measurements and insulin doses indexed by exercise events.

To illustrate the unrecognized advantage of the utilization of the preferred remote controller, two examples are set forth herein. Under screen GA7, the user or clinician can select the graphical patterns of blood glucose measurements and insulin as indexed against time in Call screen, which becomes graphical screen GGI1. Under GGI1 screen, the display provides two graphs indexed against time. A top graph in the GGI1 screen displays blood glucose measurement over time in units of mg/dL while a bottom graph displays insulin doses in Units over time. Various trends, patterns, and messages can be determined and provided to the user or health care provider using at least the blood glucose measurements and insulin doses as further described in U.S. patent application Ser. No. 11/688,639 filed on Mar. 20, 2007, which application is incorporated herein by reference. Under screen GA3, the average of all blood glucose results can be displayed in a columnar format on screen FF33.

Figure 28:
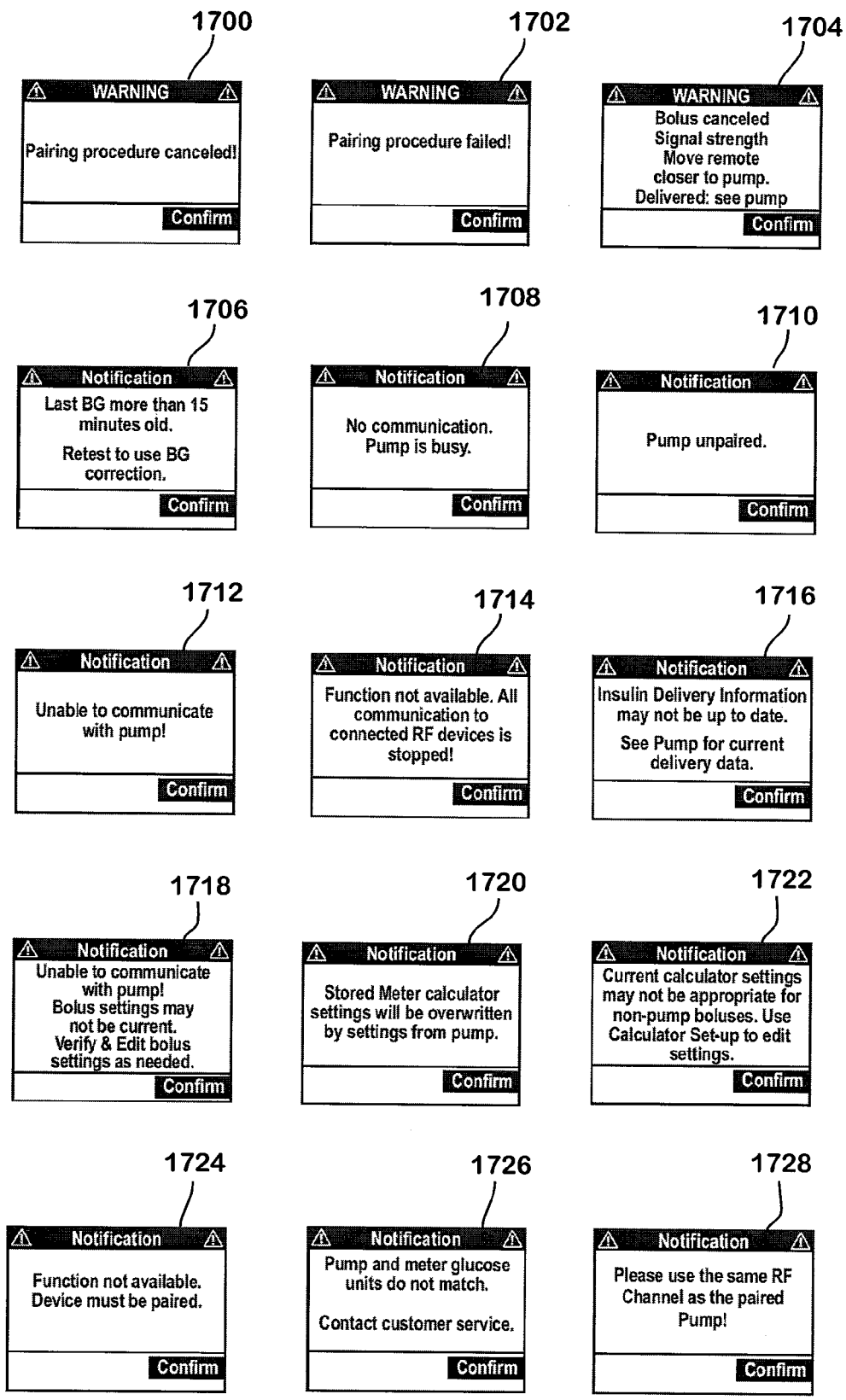
FIG. 28 illustrates a series of warning and notification screens that may be displayed on the remote controller, as used in the exemplary embodiments; and, FIG. 29 illustrates a series of medical device warning screens that are similar in layout, and may be displayed simultaneously on both the remote controller and medical device, as used in the exemplary embodiments.
Figure 29:
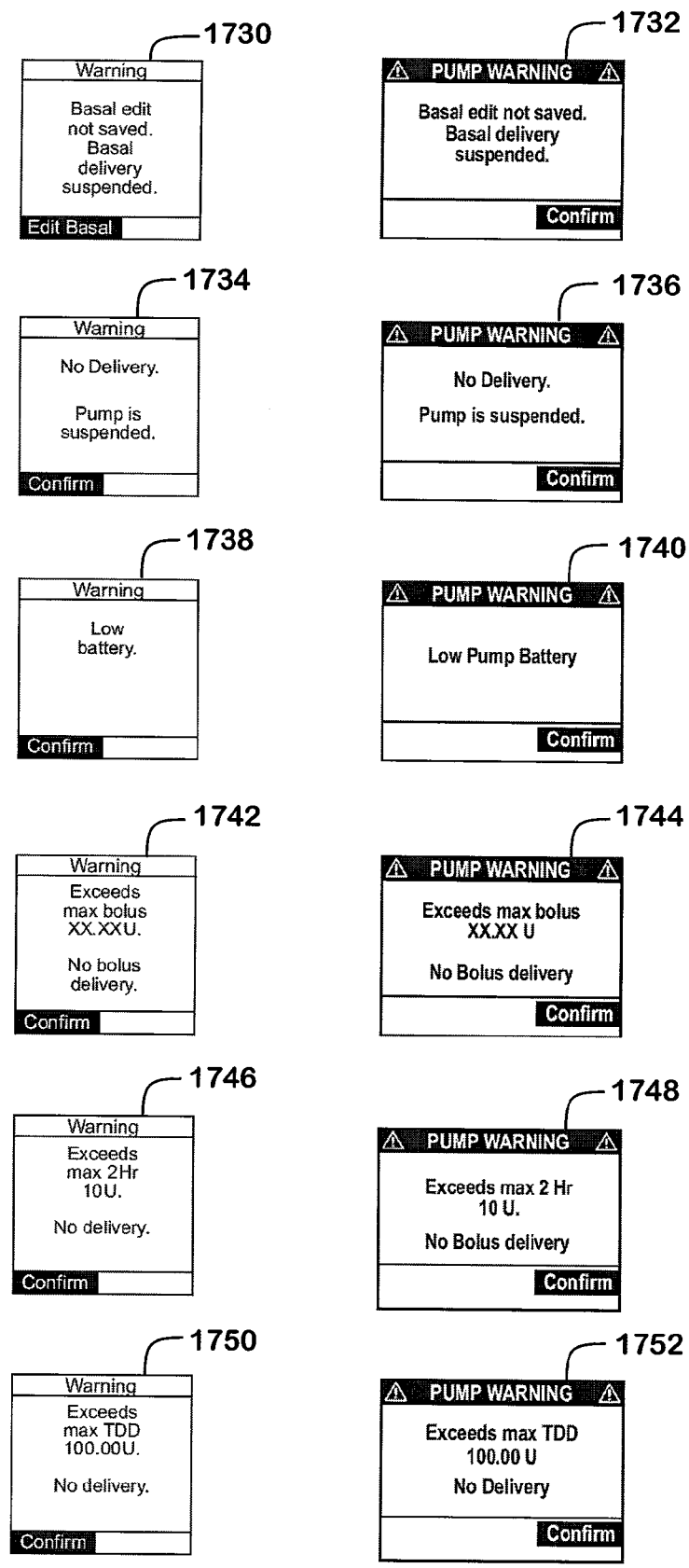

FIGS. 28 and 29 illustrate a series of warnings and notifications that are displayed on remote controller 200 and infusion pump 300. The warnings and notifications apply to operation of remote controller 200 and infusion pump 300, and to RF communication between remote controller 200 and infusion pump 300. FIG. 28 illustrates warnings and notifications that are displayed on remote controller 200, while FIG. 29 illustrates warnings that are displayed on both remote controller 200 and infusion pump 300. In respect to FIG. 28, warning screen 1700 is displayed when remote controller 200 was able to locate infusion pump 300, but the pairing procedure was canceled before it was completed. Warning screen 1702 is displayed if remote controller 200 is unable to locate infusion pump 300 during the pairing procedure. Remote controller 200 and infusion pump 300 may not be within RF range (about ~10 feet or about 3.0 meters), or pairing mode may not be activated on infusion pump 300. Warning screen 1704 is displayed when a bolus was canceled because remote controller 200 and infusion pump 300 are unable to communicate (RF is down or deactivated, remote controller 200 and infusion pump 300 are not paired, etc.). Notification screen 1706 is displayed if the last blood glucose reading was taken more than 15 minutes ago and is not current enough for use in the bolus calculator. Notification screen 1708 is displayed if communication between remote controller 200 and infusion pump 300 is suspended because infusion pump 300 is in the middle of a procedure. Notification screen 1710 is displayed if remote controller 200 and infusion pump 300 are no longer paired, and are therefore not able to communicate or share data. Notification screen 1712 is displayed if remote controller 200 and infusion pump 300 are unable to communicate. Possible causes are that remote controller 200 and infusion pump 300 are not within RF range or there is RF interference. Notification screen 1714 is displayed when remote controller 200 and infusion pump 300 are unable to communicate. A possible cause is that RF communication has been deactivated. Notification screen 1716 is displayed when delivery data on remote controller 200 may not be current because remote controller 200 and infusion pump 300 are unable to communicate. Delivery data from infusion pump 300 cannot be viewed on remote controller 200 when remote controller 200 and infusion pump 300 are unable to communicate. Notification screen 1718 is displayed when a bolus calculator has been accessed, but remote controller 200 and infusion pump 300 are unable to communicate. The bolus calculator will use values that were last set and saved on infusion pump 300. Notification screen 1720 is displayed when remote controller 200 and infusion pump 300 are paired, and bolus calculator values on remote controller 200 are replaced by those that were last saved on infusion pump 300. Notification screen 1722 is displayed when a user has chosen to unpair remote controller 200 and infusion pump 300. Notification screen 1722 warns the user that current calculator settings may not be appropriate for a bolus delivered by devices other than infusion pump 300, such as a pen or syringe. Notification screen 1724 is displayed when an attempt has been made to initiate an infusion pump function from remote controller 200 when remote controller 200 and infusion pump 300 are not currently paired. Notification screen 1726 is displayed when the glucose unit of measure on remote controller 200 and infusion pump 300 do not match. They must match for the pairing procedure to be successful. Notification screen 1728 is displayed when the RF Channel on remote controller 200 and infusion pump 300 do not match.

In FIG. 29, various infusion pump warnings are illustrated. The first column of FIG. 29 illustrates infusion pump warnings as they are displayed on remote controller 200. The second column of FIG. 29 illustrates the same warnings as they are displayed on infusion pump 300. Efforts are made to make the infusion pump warnings that appear on remote controller 200 and infusion pump 300 as similar as possible.

In one embodiment, the User Interfaces are identical for both the infusion pump 300 and remote controller 200. Applicants have recognized that this feature results in a user interface that is more intuitive and less confusing for the diabetes user who may be suffering from the effects of diabetes on their visions. In particular, warning screen 1730, warning screen 1734, warning screen 1738, warning screen 1742, warning screen 1746, and warning screen 1750 are displayed on remote controller 200, while infusion pump warning screen 1732, infusion pump warning screen 1736, infusion pump warning screen 1740, infusion pump warning screen 1744, infusion pump warning screen 1748, and infusion pump warning screen 1752 are displayed on infusion pump 300. Warning screen 1730 and infusion pump warning screen 1732 are displayed when a basal program edit has not been saved on infusion pump 300. As a result, basal delivery by infusion pump 300 stops. Warning screen 1734 and infusion pump warning screen 1736 are displayed when delivery by infusion pump 300 has been suspended. Warning screen 1738 and infusion pump warning screen 1740 are displayed when the battery in infusion pump 300 is very low, and only has about another hour of use. Warning screen 1742 and infusion pump warning screen 1744 are displayed when a new bolus command exceeds the maximum bolus limits set in infusion pump 300. In this case, the new bolus command is stopped. Warning screen 1746 and infusion pump warning screen 1748 are displayed when a new bolus command exceeds the 2-hour delivery limit that is saved in infusion pump 300. In this case, the new bolus command is stopped. Warning screen 1750 and infusion pump warning screen 1752 are displayed when a new bolus command exceeds the maximum total daily delivery limit that is saved in infusion pump 300. In this case, the new bolus command is stopped.

Although the remote controller 200 has been described in relation to a handheld unit sized for a user's hands, the remote controller 200, in an alternative embodiment, can be integrated with or implemented as part of other remote wireless device, such as, for example, a mobile phone, PDA, pager, as long as such device includes an alphanumeric display and sufficient processing power to conduct the pairing process along with the aforementioned pump controlling functions. It is believed that implementation of the mobile phone network in conjunction with the short range wireless network between the infusion pump and the remote controller allows for monitoring of therapy compliance, performance, and real-time intervention in the event that the user is undergoing a glycemic event or other issues with the pump.

It must be recognized that equivalent structures may be substituted for the structures illustrated and described herein and that the described embodiment of the invention is not the only structure that may be employed to implement the claimed invention. In addition, it should be understood that every structure described above has a function and such structure can be referred to as a means for performing that function.

While preferred embodiments of the present invention have been shown and described herein, it will be obvious to those skilled in the art that such embodiments are provided by way of example only. Numerous variations, changes, and substitutions will now occur to those skilled in the art without departing from the invention. Various alternatives to the embodiments of the invention described herein may be employed in practicing the invention. It is intended that the following claims define the scope of the invention and that methods and structures within the scope of these claims and their equivalents be covered thereby.

What is claimed is:

1. A method of operating a diabetes management system having an infusion pump and at least a remote controller, the method comprising:
   exchanging identification information of the remote controller to the infusion pump and identification information of the infusion pump to the remote controller; and
   permitting control of the infusion pump by the remote controller upon (a) acceptance of the remote controller's identification information in the infusion pump and (b) acceptance of the infusion pump's identification information in the remote controller.

2. The method of claim 1, in which the permitting comprises displaying a blank screen on a display of the infusion pump subsequent to the permitting step.

3. The method of claim 1, in which the permitting comprises transmitting the insulin sensitivity factor and target blood glucose range to the remote controller.

4. The method of claim 3, in which the permitting comprises calculating a recommendation for a bolus of insulin to be infused into a user by the infusion pump as a function of at least one of the blood glucose value, target blood glucose range, carbohydrate intake by the user, quantity of insulin delivered but not absorbed, insulin sensitivity factor, and the insulin to carbohydrate ratio at the instant of bolus recommendation.

5. The method of claim 4, in which the permitting comprises calculating a recommended bolus of insulin to be infused into a user by the infusion pump as a function of at least one of blood glucose value, target blood glucose range, quantity of insulin delivered but not absorbed, and insulin sensitivity factor.

6. The method of claim 5, in which the calculating comprises:
   determining whether a blood glucose measurement was taken within a predetermined time period prior to the calculating; and
   prompting a user of the remote controller to obtain a blood glucose measurement in the event that a blood glucose measurement was not taken in the predetermined time frame.

7. The method of claim 5, in which the calculating comprises:
   determining whether a blood glucose measurement was taken within a predetermined time period prior to the calculating; and
   utilizing a blood glucose measurement taken during the predetermined time period in the calculating of the recommended bolus.

8. The method of claim 1, further comprising logging events in the infusion pump and storing events being logged as initiated by the remote controller separate from events being logged as initiated by the infusion pump.

9. The method according to claim 8, in which the events logged include any actions initiated by the remote controller relating to one of bolus delivery, bolus cancellation, bolus or basal delivery change, suspension of infusion pump, resumption of the infusion pump, time change, alarm, or warning.

10. The method of claim 1, in which the exchanging comprises storing only one identification information of only one remote controller in the infusion pump at a given time, and only one identification information of only one infusion pump in the remote controller at a given time.

11. The method of claim 1, in which the exchanging comprises storing more than one identification information of more than one remote controller in the infusion pump.

12. The method of claim 11, further comprising permitting control of the infusion pump by a specified one of a plurality of remote controllers upon acceptance of a specified remote controller's identification information in the infusion pump and acceptance of the infusion pump's identification information in the specified remote controller.

13. The method of claim 1, further comprising displaying the remote controller's identification information on a display of the infusion pump and displaying the infusion pump's identification information on a display of the remote controller when the controller is controlling the infusion pump via a wireless link.

14. The method of claim 1, further comprising:
   utilizing a first plurality of user interfaces on the infusion pump;
   displaying on a display screen of the infusion pump a first plurality of user indicia;
   utilizing a second plurality of user interfaces essentially identical to the first plurality of user interfaces; and
   displaying on a display screen of the remote controller a second plurality of user indicia essentially identical to the first plurality of user indicia.

15. The method of claim 14, in which the displaying on the screen of the remote controller comprises:

displaying information specific only to the remote controller; and displaying information specific only to the infusion pump.

16. The method of claim 1, in which the infusion pump comprises an external insulin infusion pump carried on the body of a user.

17. The method of claim 1, in which the exchanging comprises providing a user selected indicia.

18. The method of claim 17, in which the user-selected indicia is selected from a group consisting of a user selected text nomenclature, user selected icon, user selected audio, user selected visual indicia, and combinations thereof.

19. The method of claim 1, further comprising:
displaying graphical instructions on a display screen of at least one of the remote controller and the infusion pump.

20. The method of claim 19, in which the graphical instructions comprise a series of graphical images on how to conduct at least one of a blood glucose reading and a calibration procedure.

21. The method of claim 1, further comprising:
generating vocal instructions from a speaker of at least one of the remote controller and the infusion pump.

22. The method of claim 21, in which the vocal instructions comprise a series of voice prompts on how to conduct at least one of a blood glucose reading and a calibration procedure.

* * * * *